(12) United States Patent
Cali et al.

(10) Patent No.: US 7,291,720 B2
(45) Date of Patent: Nov. 6, 2007

(54) USE OF SUBLETHAL CONCENTRATIONS OF ANTI-INVASIN COMPOUNDS TO THERAPEUTICALLY OR PROPHYLACTICALLY TREAT FUNGAL INFECTIONS

(75) Inventors: Brian Cali, Arlington, MA (US); Etchell Cordero, Reading, MA (US); Peter Hecht, Newton, MA (US); Todd Milne, Brookline, MA (US); Sofie Salama, Boston, MA (US); Eric Summers, Brookline, MA (US); Josh Trueheart, Concord, MA (US)

(73) Assignee: Microbia, Inc., Cambridge, MA (US)

( * ) Notice: Subject to any disclaimer, the term of this patent is extended or adjusted under 35 U.S.C. 154(b) by 1012 days.

(21) Appl. No.: 10/278,703

(22) Filed: Oct. 21, 2002

(65) Prior Publication Data

US 2003/0176367 A1    Sep. 18, 2003

Related U.S. Application Data

(63) Continuation of application No. 09/649,711, filed on Aug. 25, 2000, now abandoned.

(51) Int. Cl.
*C07H 21/02* (2006.01)
*C07H 21/04* (2006.01)
*A01N 43/04* (2006.01)
*A61K 31/70* (2006.01)

(52) U.S. Cl. .................................... 536/23.1
(58) Field of Classification Search ..................... None
See application file for complete search history.

(56) References Cited

U.S. PATENT DOCUMENTS 5,833,946 A    11/1998 Tamburini et al.

OTHER PUBLICATIONS

Mandels et al. J. Bacteriol. 1953 January; 65(1): 16-26.*
Alex, Lisa A. et al.; COS1, a two-component histidine kinase that is involved in hyphal development in the opportunistic pathogen *Candida albicans*; Proc. Natl. Acad. Sci. USA 95: 7069-7073 (1998).
Alonso-Monge, R. et al.; Role of the Mitogen-Activated Protein Kinase Hog1p in Morphogenesis and Virulence of *Candida albicans*; J. Bacteriology, 181: 3058-3068 (1999).
Baillie, George A., et al.; Candida Biofilms and Their Susceptibility to Antifungal Agents; Methods in Enzymology 310: 644-656 (1999).
Braga, P.C., et al.; Effects of Subinhibitory Concentrations of Ciclopirox on the Adherence of *Candida albicans* to Human Buccal and Vaginal Epithelial Cells;Antimycotics-Fungicides 42: 1368-1371 (1992).
Braga, P.C., et al.; Experimental Evidences for a Role of Subinhibitory Concentrations of Rilopirox, Nystatin and Fluconazole on Adherence of Candida spp. to Vaginal Epithelial Cells; Chemotherapy 42: 259-265 (1996).
Bremm, K. D., et al.; Influence of Azole Componds on Adhesion, Germ Tube Formation and Virulance of *C. albicans* in Cell Cultures and Infected Animals; Candida and Candidamycosis (E. Tumbay, Ed.), 97-100; Plenum Press, New York (1991).
Brenciaglia, M. I., et al.; The Influence of Antifungal Drugs on Adherence of *Candida albicans* to Buccal Epithelial Cells; Chemioterapia 5: 200-203 (1986).
Calera, Jose Antonio, et al.; Defective Hyphal Development and Avirulence Caused by a Deletion of the SSK1 Response Regulator Gene in *Candida albicans*; infection and Immunity 68: 518-525 (2000.
Csank, Csilla, et al.; Roles of the *Candida albicans* Mitogen-Activated Protein Kinase Homolog, Cek1p, in Hhphal Development and Systemic Candidiasis; Injection and Immunity 66: 2713-2721
Ellepola, A. N. B., et al.; Adhesion of oral *C. albicans* to human buccal epithelial cells following limted exposure to antifungal agents; J. Oral Pathol. Med. 27: 325-332 (1998).
Ellepola, A. N. B. , et al.; Adhesion of oral *Candida albicans* isolates to denture acrylic following limted exposure to antifungal agents; Arch. Oral. Biol. 43:999-1007 (1998.
Ellepola, A. N. B., et al; The effect of limited exposure to antifungal agents on the germ tube formation of oral *Candida albican*; J. Oral Pathol. Med. 27: 213-219 (1998).
Ghannoum, Mahmound A., et a;.; Modulation of Interactions of *Candida albicans* and Endothelia Cells by Fluconazole and Amphotericin B; Antimicrobia Agents Chemotherapy; 36:2239-2244. (1992).
Ha, Kien C., et al.; Effects of Azole Antifungal Drugs on the Transition from Yeast Cells to Hyphae in Susceptible and Resistant Isolates of the Pathogenic Yeast *Candida albicans*; Antimicrobial Agents and Chemotherapy 43: 763-768 (1999).
Haller, Ingo: Mode of action of clotrimazole: Implications for therapy; Am. J. Obstet, Gynecol. 152: 939-944 (1985).
Hawser, Stepen, et al.; The effects of antigual agents on the morphogentic transformation by *Candia albicans* in vitro; J. Antimicrob. Chemother. 38: 579-587 (1996).

(Continued)

*Primary Examiner*—Patrick Lewis
(74) *Attorney, Agent, or Firm*—Fish & Richardson P.C.

(57) ABSTRACT

The invention relates to the therapeutic or prophylactic treatment of fungal infections. The invention provides new methods for therapeutically or prophylactically treating fungal infections using sub-lethal concentrations of an anti-invasin compound. The methods according to the invention have fewer toxicology problems than existing methods, and thus can be used prophylactically, as well as for early treatment for high risk patients without a firm diagnosis. The methods according to the invention can also be used to treat an established fungal infection. The invention further provides novel genes that regulate fungal hyphal growth.

8 Claims, 48 Drawing Sheets

OTHER PUBLICATIONS

Hawser, Stephen, et al.; Comparisons of the effects of fungicidal and fungistatic antifungal agents on the morphogenetic transformation of *Candida albicans*; J. Antimicrob. Chemother. 43: 411-413 (1999).

Kretschmar, Marianne, et al.; Germ Tubes and Proteinase Activity Contribute to Virulence of *Candida albicans* in Murine Peritonitis; Infection and Immunity 67: 6637-6642 (1999).

Lo, Hsiu-Jung, et al.; Nonfilamentous *C. albicans* Mutants Are Avirulent; Cell 90: 939-949 (1997).

Martin, Michael V.; The use of fluconazole and itraconazole in the treatment of *Candida albicans* infections: a review; J. Antimicrob. Chemother. 44: 429-437 (1999).

Mehentee, J.F., et al.; Effect of antifungal agents on the adherence of *Candida albicans* to murine gastrointestinal mucosal surfaces; J. Antimicrob. Chemother. 25: 111-119 (19900.

Nugent, Kenneth M., et al.; Effects of Sublethal Concentrations of Amphotericin B on *Candida albicans*; J. Infect. Dis. 154: 665-669 (1986).

Norman, Thea C., et al.; Genetic Selection of Peptide Inhibitors of Biological Pahthways; 285: 591-595 (1999).

Philpott-Howard, J. N.; et al.; Randomized comparison of oral fluconazole versus oral polyenes for the prevention of fungal infection in patients at risk of neutropenia: J. Antimicrob. Chemother. 31: 973-984 (1993).

Plempel, M., et al.; Reduction of the In Vivo Virulence of *Candida albicans* by Pretreatment with Subinhibitory Azole Concentrations In Vitro; Dermatologica 169: Suppl. 1.11-18 (1984).

Staab, Janet F., et al.; Developmental Expression of a Tandemly Repeated, Proline-and Glutamine-rich Amino Acid Motif on Hyphal Surfaces of *Candida albicans*; J. Biological Chemistry 271: 6298-6306 (1996).

Van't Wout, Jan W., et al.; Effect of amphotericin B, fluconazole and intraconazole on intracellular *Candida albicans* and germ tube development in macrophages; J. Antimicrob, Chemother. 25: 803-811 (1990).

Weig, Michael, et al.; Clinical aspects and pathogenesis of Candida infection; Trends in Microbiology 6: 468-470 (1998).

Braga et al., "Inhibition of *Candida albicans* Adhesiveness to Human Buccal and Vaginal Cells . . . " Arzneimittel Forschung. Drug Research, Editio Cantor. Aulendorf, DE, vol. 45:84-87, 1995.

Haller, I., "Zum Wirkengstyp von Imidazol-Antimykotika: Konsequenzen fur die . . . " Mykosen 22:423-430, 1979.

Macura, A/. "The Influence of Some Antifungal Drugs on In Vitro Adherence of *Candida albicans* to Human . . . " Mycoses 31:371-376, 1988.

Nosanchuk et al., "Amphotericin B and Fluconazole Affect Cellular Charge, Macrophage Phagocytosis, . . . " Antimicrobial Agents and Chem. 43:233-239, 1999.

Osumi et al., "The Effect of Bifonazole on the Structure of Trichophyton" Arzneimittel-Forschung, Germany 33:1484-1491, 1983.

Schaude et al., "Inhibitory Effect of Antifungal Agents on Germ Tube Formation in *Candida albicans*" Mykosen 30:281-287, 1987.

Teen et al., "Effects of Sub-Inhibitory Concentrations of Antifungal Agents on Adherence of . . . " Mycoses 32:551-562, 1989.

Wills et al., "New Potential Targets for Antifungal Development" Emerging Therapeutic Targets 4:1-32, 2000.

* cited by examiner

|     |     |
| --- | --- |
| FIG. 1A | |
| FIG. 1B | |
| FIG. 1C | |
| FIG. 1D | |
| FIG. 1E | |
| FIG. 1F | |
| FIG. 1G | |
| FIG. 1H | |
| FIG. 1I | |
| FIG. 1J | |
| FIG. 1K | |
| FIG. 1L | |
| FIG. 1M | |

FIG. 1

CRV1 ORF 82400

```
    +1  M  N  H  K  Q  V  L  P  E  N  E  P  I  S  T  T  T
     1  ATGAATCATA AACAAGTACT TCCAGAAAAT GAACCGATAT CAACAACAAC
        TACTTAGTAT TTGTTCATGA AGGTCTTTTA CTTGGCTATA GTTGTTGTTG

+1  A  T  P  S  S  S  N  T  M  V  P  N  T  T  K  Q
    51  AGCAACTCCA TCATCATCCA ATACTATGGT TCCCAACACA ACTAAACAGG
        TCGTTGAGGT AGTAGTAGGT TATGATACCA AGGGTTGTGT TGATTTGTCC

+1  V  L  N  S  L  I  L  D  F  L  V  K  H  Q  F  Q  D
   101  TTTTAAACTC GTTGATTTTG GATTTTTTGG TCAAACATCA ATTTCAAGAT
        AAAATTTGAG CAACTAAAAC CTAAAAAACC AGTTTGTAGT TAAAGTTCTA

+1  T  A  K  A  F  S  K  E  S  P  N  L  P  S  I  P  P
   151  ACAGCAAAAG CATTTCTAA AGAAGTCCC AATTGCCTT CTATTCCTCC
        TGTCGTTTTC GTAAAGATT TCTTTCAGGG TTAAACGGAA GATAAGGAGG
```

FIG. 1A

```
+1        L   M   D   C   S   Q   G   F   L   L   E   W   W   Q   V   F
          ---]-------------------------------------------------------------
201       TTGATGGAT TGTTCTCAAG GATTTTTATT GGAATGGTGG CAAGTTTTCT
          AAACTACCTA ACAAGAGTTC CTAAAAATAA CCTTACCACC GTTCAAAAGA

+1        F   D   L   F   Q   V   R   Y   G   D   G   N   S   N   N   P
          ------------------------------------------------------------------
251       TTGATTTATT TCAAGTCAGA TATGGAGACG GTAACAGTAA TAATAACCCT
          AACTAAATAA AGTTCAGTCT ATACCTCTGC CATTGTCATT ATTATTGGGA

+1        N   N   K   L   Y   H   D   Y   L   R   V   Q   E   T   Q   K   H
          ---------------------------------------------------------------------
301       AACAACAAGC TTTATCATGA TTATCTCAGA GTCCAAGAAA CTCAAAAACA
          TTGTTGTTCG AAATAGTACT AATAGAGTCT CAGGTTCTTT GAGTTTTTGT

+1        L   F   S   Q   L   P   L   I   Q   Q   Q   Q   Q   Q   Q   H
          ------------------------------------------------------------------
351       TCTTTTCAGT CAACTTCCCT CTTATACAGCA GCAGCAACAA CAACAACATC
          AGAAAAGTCA GTTGAAGGAG AATATGTCGT CGTCGTTGTT GTTGTTGTAG
```

FIG. 1B

+1    H   F   Q   Q   Q   Q   Q   Q   Q   Q   Q   Q   G   Q   Q   Q   P   F   L
401   ACTTTCAACA ACAACAGCAA CAACAAGGGC AACAGGGACA GCCTTTCCTG
      TGAAAGTTGT TGTTGTCGTT GTTGTTCCCG TTGTCCCTGT CGGAAAGGAC

+1    Q   Q   Q   Q   Q   R   G   I   G   V   A   S   G   M   Q   N   Q   Q
451   CAGCAACAGC AAAGAGGAAT CGGTGTTGCT AGTGGTATGC AAAATCAACA
      GTCGTTGTCG TTTCTCCTTA GCCACAACGA TCACCATACG TTTTAGTTGT

+1    H   Q   F   A   P   Q   H   Q   G   Q   P   Q   G   P   G   Q
501   ACATCAATTT GCCCCACAGC ATCAAGGCCA ACCTCAAGGA CCAGGTCAAA
      TGTAGTTAAA CGGGGTGTCG TAGTTCCGGT TGGAGTTCCT GGTCCAGTTT

+1    T   P   Q   P   P   G   S   A   T   N   A   N   F   P   I   N   M
551   CACCTCAACC GCCAGGTTCT GCAACTAACG CTAATTTCCC TATCAATATG
      GTGGAGTTGG CGGTCCAAGA CGTTGATTGC GATTAAAGGG ATAGTTATAC

FIG. 1C

```
+1    P   P   N   L   N   P   Q   Q   Q   M       F   P   I   N   Q   Q   F
      -------------------------------]-----------------------------------
601   CCACCAAATC TGAATCCTCA ACAACAAATG TTCCCCATTA ATCAACAATT
      GGTGGTTTAG ACTTAGGAGT TGTTGTTTAC AAGGGGTAAT TAGTTGTTAA

+1    A   Q   M       P   N   G   Q   N   Q   P       S   M   E   Q   Q   Q
      ------------]---------------------------]-----------------------------
651   TGCTCAGATG CCAAATGGTC AAAATCAGCC TTCAATGGAA CAACAACAAA
      ACGAGTCTAC GGTTTACCAG TTTTAGTCGG AAGTTACCTT GTTGTTGTTT

+1    R   M   A   M   M   K       Q   Q   A   M       A   A   Q       R   Q   Q
      --]-----------------]---------------------]---------------]---------------
701   GAATGGCAAT GATGATGAAA CAACAAGCAA TGGCTGCACA AAGACAACAA
      CTTACCGTTA CTACTACTTT GTTGTTCGTT ACCGACGTGT TTCTGTTGTT

+1    I   I   P   M   N       G   L   D   P   Q   Q       Q   Q   Q   M   N   A
      ----------------]------------------------]-------------------------------
751   ATCCCAATGA ATGGTTTAGA TCCACAACAA CAACAGCAAA TGAATGAATGC
      TAGGGTTACT TACCAAATCT AGGTGTTGTT GTTGTCGTTT ACTACTTACG
```

FIG. 1D

```
+1      V   G   G   G   P   G   N   L   N   L   Q   Q   Q   Q   L   F   L
                                          -----------------------
801   TGTAGGTGGT GGACCTGGTA ATTTGAATTT GCAACAACAA CTATTTTTAC
      ACATCCACCA CCTGGACCAT TAAACTTAAA CGTTGTTGTT GATAAAAATG

+1      Q   Q   Q   Q   Q   Q   Q   Q   Q   P   K   T   F   Q   Q   Q   A
      ---------------------------------------------              -
851   AACAACAACA GCAGCAGCAG CAACCCAAAA CTACTTTCCA GCAACAAGCA
      TTGTTGTTGT CGTCGTCGTC GTTGGGTTTT GATGAAAGGT CGTTGTTCGT

+1      Q   N   Q   M   N   N   L   R   Q   Q   A   A   M   V   A   Q   Q
                        ---------------             ---------
901   CAAAATCAAA TGAACAATTT GCGTCAACAA GCTGCAATGG TTGCTCAGCA
      GTTTTAGTTT ACTTGTTAAA CGCAGTTGTT CGACGTTACC AACGAGTCGT

+1      Q   Q   Q   Q   Q   Q   Q   Q   Q   Q   Q   Q   Q   L   Q   G
                                                               -
951   GCAGCAACAG CAACAGCAAC AGCAACAACA ACAGGGTCAG TTGCAAGGCA
      CGTCGTTGTC GTTGTCGTTG TCGTTGTTGT TGTCCCAGTC AACGTTCCGT
```

FIG. 1E

```
     +1  N   L   T   S   A   M   G   D   S   S   L   K   N   N   S   P   V
         ---------------------------------]----------------------------------
 1001    ATTGACATC AGCAATGGGT GATTCATCTC TGAAGAATAA CTCTCCTGTT
         TAAACTGTAG TCGTTACCCA CTAAGTAGAG ACTTCTTATT GAGAGGACAA

+1  G   A   R   S   N   Q   Q   L   T   P   Q   Q   N   A   A   P   A
         -----------------------------------------------------------------
 1051    GGTGCAAGAT CAAATCAACA GCTGACTCCA CAACAAAATG CTGCACCAGC
         CCACGTTCTA GTTTAGTTGT CGACTGAGGT GTTGTTTTAC GACGTGGTCG

+1  S   L   P   H   P   S   Q   Q   G   Q   A   Q   A   Q   H   N
         --------------------------------------------------------------
 1101    TTCACTGCCA CATCCTTCTC AACAAGGTCA AGCACAAGCT CAACATAACT
         AAGTGACGGT GTAGGAAGAG TTGTTCCAGT TCGTGTTCGA GTTGTATTGA

+1  F   Q   S   H   Q   Q   Q   Q   Q   Q   Q   M   T   K   M   A   G   S
         -------------------------------]----------------------------------
 1151    TCCAGAGCCA TCAACAACAA CAACAGCAAA TGACTAAGAT GGCTGGGTCT
         AGGTCTCGGT AGTTGTTGTT GTTGTCGTTT ACTGATTCTA CCGACCCAGA
```

FIG. 1F

```
+1         Q  G  M  K  K  N  G    Q  M  S    N  G  T  S    N  N  S
           -------------]---------------]--------------]---------
1201       CAAGGAATGA AAAGAATGG TCAGATGTCA AACGGCACTA GTAATAACAG
           GTTCCTTACT TTTCTTACC AGTCTACAGT TTGCCGTGAT CATTATTGTC

+1         S  G  R    N  N  N  A  L  R  D    Y  Q  N    Q  L  M
           -----------------------------]-----------------------]--
1251       TAGTGGCAGA AACAATAAATG CTCTACGAGA TTATCAAAAT CAATTAATGT
           ATCACCGTCT TTGTTATTAC GAGATGCTCT AATAGTTTTA GTTAATTACA

+1         L  L  E  R    Q  N  K    E  R  L  E    F  A  R    N  T  G
           -------------------------------------------------]--------
1301       TATTAGAAAG ACAGAATAAA GAGAGATTAG AATTTGCTAG AAACACTGGT
           ATAATCTTTC TGTCTTATTT CTCTCTAATC TTAAACGATC TTTGTGACCA

+1         N  S  D  S    N  P  L    S  N  G    M  M  F  A  G  Q  N
           ------------------------------]---------------------------
1351       AATTCCGACT CCAACCCATT GAGTAATGGA ATGATGTTTG CCGGTCAAAA
           TTAAGGCTGA GGTTGGGTAA CTCATTACCT TACTACAAAC GGCCAGTTTT
```

FIG. 1G

```
+1       Q   Y   S   N   S   N   Q   N   Q   L   P   P   N   Q
1401   TCAATATTCA AATTCAAATC AAAATCAAAA TCAACTTCCT CCTAATCAAC
       AGTTATAAGT TTAAGTTTAG TTTTAGTTTT AGTTGAAGGA GGATTAGTTG

+1       Q   Q   P   T   P   A   T   F   H   P   P   P   P   T   T   A
1451   AACAACCAAC TCCAGCAACT TTCCACCCAC CACCTCCGCC AACAACTGCA
       TTGTTGGTTG AGGTCGTTGA AAGGTGGGTG GTGGAGGCGG TTGTTGACGT

+1       N   G   P   Q   G   Q   F   N   Q   K   P   S   P   A   T   S   N
1501   AATGGTCCTC AGGGACAATT TAATCAAAAA CCATCACCTG CAACGTCAAA
       TTACCAGGAG TCCCTGTTAA ATTAGTTTTT GGTAGTGGAC GTTGCAGTTT

+1       N   S   P   A   L   G   N   K   S   S   P   A   M   G   N   K
1551   CAATTCACCT GCATTAGGCA ATAAATCATC ACCAGCAATG GGCAATAAGA
       GTTAAGTGGA CGTAATCCGT TATTTAGTAG TGGTCGTTAC CCGTTATTCT
```

FIG. 1H

```
+1   K  S  K  K  E  S  N  S  K  K  G  K  K  A  N  S  N
     -  -  -  -  -  -  -  -  -  -  -  -  -  -  -  -  -
1601 AATCGAAGAA AGAATCCAAT AGTAAAAAGG GTAAAAAGGC GAATTCAAAT
     TTAGCTTCTT TCTTAGGTTA TCATTTTTCC CATTTTTCCG CTTAAGTTTA
```

```
+1   A  S  T  T  A  N  N  K  T  S  G  Q  T  T  P  N  M
     -  -  -  -  -  -  -  -  -  -  -  -  -  -  -  ]  -
1651 GCTTCTACAA CAGCAAACAA CAAAACATCT GGACAAACAA CACCAAACAT
     CGAAGATGTT GTCGTTTGTT GTTTTGTAGA CCTGTTTGTT GTGGTTTGTA
```

```
+1   S  Q  P  P  S  A  G  T  E  Q  K  Q  P  Q  P  T
     -  -  -  -  -  -  -  -  -  -  -  -  -  -  -  -
1701 GTCACAACCT CCTAGTGCTG GCACGGAGCA AAAGCAGCCT CAACCAACAG
     CAGTGTTGGA GGATCACGAC CGTGCCTCGT TTTCGTCGGA GTTGGTTGTC
```

```
+1   E  Q  M  R  Q  L  Q  D  K  Q  Q  R  P  G  S  N  T
     -  -  ]  -                -  -  -  -  -  -  -  -  -
1751 AGCAAATGCG TCAATTACAA GACAAGCAAC AGCGTCCAGG TTCAAATACT
     TCGTTTACGC AGTTAATGTT CTGTTCGTTG TCGCAGGTCC AAGTTTATGA
```

FIG. 11

```
+1       P   S   M   G   K   K   D   F   Q   P   L   T   P   R   S   E   P
         ---------------------------------------------------------------]
1801     CCAAGTATGG GAAAGAAGGA TTTCCAGCCA TTGACACCTC GCTCTGAACC
         GGTTCATACC CTTTCTTCCT AAAGGTCGGT AACTGTGGAG CGAGACTTGG

+1       I   S   G   E   T   T   K   K   K   R   K   S   G   K   L   N
1851     AATTAGCGGT GAAACTACGA AAAAGAAGCG TAAATCAGGT AAATTGAATG
         TTAATCGCCA CTTTGATGCT TTTTCTTCGC ATTTAGTCCA TTTAACTTAC

+1       D   N   N   E   N   S   N   G   N   S   P   K   K   Q   A   K   T
1901     ACAATAATGA AAATAGTAAT GGCAATTCTC CAAAGAAGCA AGCCAAAACC
         TGTTATTACT TTTATCATTA CCGTTAAGAG GTTTCTTCGT TCGGTTTTGG

+1       N   A   N   S   K   N   L   D   P   I   K   E   E   E   N   G
1951     AATGCAAACT CCAAAAACTT AGATCCTATA ATAAAGAAG AAGAGAATGG
         TTACGTTTGA GGTTTTTGAA TCTAGGATAT TATTTTCTTC TTCTCTTACC
```

FIG. 1J

```
   +1       V   L   S   L   K   K   E   S   S   T   S   L   Q   D   Q   D
                -----------------------------------------------------------------
   2001    AGTATTATCT TGAAGAAAG AATCTTCAAC TTCGTTACAA GATCAAGATC
           TCATAATAGA AACTTCTTTC TTAGAAGTTG AAGCAATGTT CTAGTTCTAG

+1       L   D   L   N   P   P   L   A   P   T   Q   A   T   A   M   S   N
                -----------------------------------------------------------------
   2051    TAGATTTAAA CCCCCCATTG GCACCAACTC AAGCCACTGC TATGTCCAAT
           ATCTAAATTT GGGGGGTAAC CGTGGTTGAG TTCGGTGACG ATACAGGTTA

+1       T   F   N   D   D   P   F   D   V   H   L   L   D   T   Q   H   H
                -----------------------------------------------------------------
   2101    ACATTAACG ACGATCCATT TGATGTTCAT TTATTAGATA CACAACATCA
           TGTAAATTGC TGCTAGGTAA ACTACAAGTA AATAATCTAT GTGTTGTAGT

+1       H   Q   Q   N   S   N   N   S   N   H   N   R   G   Q   N   L
                -----------------------------------------------------------------
   2151    TCACCAACAA AATAGCAATCA ACAGCAATCA TAATCGTGGG CAAAATCTTT
           AGTGGTTGTT TTATCGTTAGT TGTCGTTAGT ATTAGCACCC GTTTTAGAAA
```

FIG. 1K

```
     +1  S  N  G  S   N  N  L   S  V  S  G   P  G  M   G  M  N
         CAAATGGAAG TAATAATCTC AGTGTAAGTG GCCCAGGAAT GGGAATGAAT
   2201  GTTTACCTTC ATTATTAGAG TCACATTCAC CGGGTCCTTA CCCTTACTTA

+1  N  L  V  F   G  D  S   T  H  A   F  D  I  N   F  N  I
         AATCTGGTAT TTGGTGATTC GACTCATGCA TTTGACATTA ATTTCAACAT
   2251  TTAGACCATA AACCACTAAG CTGAGTACGT AAACTGTAAT TAAAGTTGTA

+1  D  S  L   D  D  I  W   T  T  T   G  P  G   G  D  I
         TGATAGTCTT GATGATATAT GGACAACTAC TGGACCAGGA GGTGATATTA
   2301  ACTATCAGAA CTACTATATA CCTGTTGATG ACCTGGTCCT CCACTATAAT

+1  T  G  T  G   S  G  S   G  G  A  G   G  T  D   D  D  N
         CTGGCACTGG TTCGGGTTCA GGAGGTGCTG GCGGTACCGA TGATGATAAC
   2351  GACCGTGACC AAGCCCAAGT CCTCCACGAC CGCCATGGCT ACTACTATTG
```

FIG. 1L

+1    F   M   G   M   N   W   A   A   D   P   I   E   N   G   D
      ------------------------------------------------------------>
2401  TTCATGGGAA TGAATTGGGC TGCAGATCCA ATTGAAAATG GAGATTAG
      AAGTACCCTT ACTTAACCCG ACGTCTAGGT TAACTTTTAC CTCTAATC

FIG. 1M

| | |
|---|---|
| | FIG. 2A |
| | FIG. 2B |
| | FIG. 2C |
| | FIG. 2D |
| | FIG. 2E |
| | FIG. 2F |
| | FIG. 2G |
| | FIG. 2H |
| | FIG. 2I |
| | FIG. 2J |
| | FIG. 2K |
| | FIG. 2L |

FIG. 2

CRV2 ORF

```
+1    M  M  S  Q  A  T  P  S  A  T  P  V  R  N  A  D  G
      ]--]----------------------------------------------
  1   ATGATGTCGC AAGCTACTCC TAGTGCTACT CCCGTGAGAA ATGCCGATGG
      TACTACAGCG TTCGATGAGG ATCACGATGA GGGCACTCTT TACGGCTACC

+1    Q  K  K  G  K  K  L  P  L  I  V  D  V  A  I  G
      -----------------------------------------------
 51   ACAAAAGAAA GGCAAGAAGC TTCCATTAAT TGTTGATGTT GCAATTGGTA
      TGTTTTCTTT CCGTTCTTCG AAGGTAATTA ACAACTACAA CGTTAACCAT

+1    N  N  G  K  Q  L  Y  Q  V  H  E  S  S  K  M  V  R
      ]----------------------------------------------]---
101   ATAATGGTAA GCAACTTTAC CAGGTACACG AATCTTCCAA GATGGTAAGA
      TATTACCATT CGTTGAAATG GTCCATGTGC TTAGAAGGTT CTACCATTCT

+1    K  E  M  P  R  S  T  N  F  A  L  N  D  D  I  S  D
      --------]------------------------------------------
151   AAGGAAATGC CAAGATCTAC CAATTTGCT TTGAATGATG ACATTTCTGA
      TTCCTTTACG GTTCTAGATG GTTAAAACGA AACTTACTAC TGTAAAGACT
```

FIG. 2A

```
+1        E   G   F   F   I   S   Q   I   N   E   Q   R   T   P   I   R
201   TGAAGGGTTT TTTATAAGCC AAATAAATGA ACAAAGAACT CCCATTAGAA
      ACTTCCCAAA AAATATTCGG TTTATTTACT TGTTTCTTGA GGGTAATCTT

+1        K   T   L   G   T   L   S   P   S   S   L   N   Q   K   R   I   R
251   AGACTTTGGG TACTTTGTCT CCATCTAGTC TCAACCAAAA GAGAATCCGC
      TCTGAAACCC ATGAAACAGA GGTAGATCAG AGTTGGTTTT CTCTTAGGCG

+1        H   D   V   Y   D   Q   G   D   D   N   S   N   D   D   N   C   Q
301   CATGATGTGT ACGACCAAGG AGATGACAAT AGCAATGACG ATAATTGCCA
      GTACTACACA TGCTGGTTCC TCTACTGTTA TCGTTACTGC TATTAACGGT

+1        N   D   V   Y   E   Q   Q   Q   Q   Q   Q   P   Q   Q   Q   Q   Q
351   AAATGATGTT TATGAGCAAC AACAACAACA ACCACAGCAA CAACAACAAC
      TTTACTACAA ATACTCGTTG TTGTTGTTGT TGGTGTCGTT GTTGTTGTTG
```

FIG. 2B

```
+1    Q  Q  Q  Q    L  H  Q    P  N  M  Y    E  N  G    N  V  G
      |--------|    |-----|    |--------|    |-----|    |-----|
401   AACAACAACA    ACTTCATCAA CCTAATATGT    ATGAGAACGG CAACGTTGGG
      TTGTTGTTGT    TGAAGTAGTT GGATTATACA    TACTCTTGCC GTTGCAACCC

+1    V  I  S  N    D  P  V    S  S  V    G  H  Y  D    N  N  P
      |--------|    |-----|    |-----|    |--------|    |-----|
451   GTTATTTCCA    ATGATCCAGT GTCTTCTGTT GGCCACTATG    ACAACAACCC
      CAATAAAGGT    TACTAGGTCA CAGAAGACAA CCGGTGATAC    TGTTGTTGGG

+1    V  S  H    V  P  T    G  A  Y  S    R  V  Q    D  T  D
      |-----|    |-----|    |--------|    |-----|    |-----|
501   AGTTCACAT  GTACCTACTG  GTGCTTATTC  ACGTGTCCAA  GACACTGACA
      TCAAAGTGTA CATGGATGAC  CACGAATAAG  TGCACAGGTT  CTGTGACTGT

+1    I  W  S  D    D  V  E    E  A  F    E  E  V  L    R  L  I
      |--------|    |-----|    |-----|    |--------|    |-----|
551   TCTGGTCAGA    TGATGTTGAA GAAGCTTTTG AAGAAGTGTT    GAGACTTATT
      AGACCAGTCT    ACTACAACTT CTTCGAAAAC TTCTTCACAA    CTCTGAATAA
```

FIG. 2C

```
+1       P   K   S   G   L   N   K   I   K   I   A   G   R   S   C   G   R
601      CCAAAGAGTG GTTGAACAA AATAAAGATT GCCGGTAGAT CTTGTGGTAG
         GGTTTCTCAC CAAACTTGTT TTATTTCTAA CGGCCATCTA GAACACCATC

+1       N   E   L   I   S   D   Y   I   F   A   K   T   G   K   F   R
651      AAATGAATTA ATATCAGATT ACATTTTTGC CAAAACCGGG AAATTCAGAA
         TTTACTTAAT TATAGTCTAA TGTAAAAACG GTTTTGGCCC TTTAAGTCTT

+1       T   R   K   Q   V   S   S   H   I   Q   V   I   K   N   L   G   Q
701      CAAGAAAGCA AGTGTCCTCT CACATTCAAG TGATTAAGAA TTTAGGACAA
         GTTCTTTCGT TCACAGGAGA GTGTAAGTTC ACTAATTCTT AAATCCTGTT

+1       K   L   D   I   I   Q   L   I   N   D   G   P   I   F   N   S   H
751      AAACTCGATA TAATCCAATT GATCAACGAT GGTCCTATTT TCAACAGTCA
         TTTGAGCTAT ATTAGGTTAA CTAGTTGCTA CCAGGATAAA AGTTGTCAGT
```

FIG. 2D

```
+1        E   E   Q   L   E   S   T   K   K   F   E   D   V   F   S   K
801       CGAGGAACAA TTGGAATCAA CCAAGAAATT TGAAGATGTT TTTCGAAAA
          GCTCCTTGTT AACCTTAGTT GGTTCTTTAA ACTTCTACAA AAAAGCTTTT

+1        I   I   N   L   N   K   S   L   G   F   S   D   S   M   K   R   K   S
851       TTAATTTGAA CAAGTCACTT GGGTTTAGTG ACTCGATGAA AAGAAAAAGT
          AATTAAACTT GTTCAGTGAA CCCAAATCAC TGAGCTACTT TTCTTTTTCA

+1        D   S   M   P   M   H   L   P   A   T   K   R   I   R   R   K   H
901       GATTCAATGC CTATGCATCT CCCAGCCACA AAGAGAATAA GAAGAAAACA
          CTAAGTTACG GATACGTAGA GGGTCGGTGT TTCTCTTATT CTTCTTTTGT

+1        S   G   N   P   L   N   K   I   K   F   S   N   F   F   M   S
951       CTCGGGCAAT CCTTTGAATA AAATAAAAATT TAGCAATTTC TTCATGTCTG
          GAGCCCGTTA GGAAACTTAT TTTATTTTAA ATCGTTAAAG AAGTACAGAC
```

FIG. 2E

```
   +1  V  N  D  Q  Y  G  M  N  P  I  V  L  T  I  Q  Q  N
       ------------------------------------------]
1001   TTAATGACCA ATACGGTATG AATCCAATTG TTTGACGAT ACAGCAAAAT
       AATTACTGGT TATGCCATAC TTAGGTTAAC AAAACTGCTA TGTCGTTTTA

+1  G  N  D  V  K  S  L  K  L  K  D  N  A  N  I  S  S
       ---------------------------------------------------
1051   GGCAATGACG TTAAAGTTT GAAATTGAAA GACAATGCTA ATATTTCCAG
       CCGTTACTGC AATTTCAAA CTTTAACTTT CTGTTACGAT TATAAAGGTC

+1  R  F  P  G  L  S  D  F  K  S  C  P  H  I  P  I
       ----------------------------------------------
1101   TAGGTTCCCT GGTTTAAGTG ATTTTAAATC GTGTCCTCAT ATTCCAATCA
       ATCCAAGGGA CCAAATTCAC TAAAATTTAG CACAGGAGTA TAAGGTTAGT

+1  I  I  H  N  M  V  K  I  L  L  P  Q  L  P  E  S  Y  S
       ------------]---]------------------------------------
1151   TTCACAACAT GGTGAAAATA TTGCTCCCGC AGTTGCCAGA ATCATATAGT
       AAGTGTTGTA CCACTTTTAT AACGAGGGCG TCAACGGTCT TAGTATATCA
```

FIG. 2F

```
+1    I   D   D   G   F   S   S   S   Y   A   L   K   Y   E   E   P   E
1201  ATCGACGACG GGTTAGTTC CAGTTATGCT TTGAAGTACG AAGAACCAGA
      TAGCTGCTGC CCAAATCAAG GTCAATACGA AACTTCATGC TTCTTGGTCT

+1    N   A   S   P   T   H   T   S   I   I   S   S   S   R   T   Y
1251  AAACGCATCA CCCACACATA CCAGTATTAT ATCATCTTCT AGAACTTACA
      TTTGCGTAGT GGGTGTGTAT GGTCATAATA TAGTAGAAGA TCTTGAATGT

+1    S   L   F   T   C   V   Y   S   Y   G   K   E   I   V   K   F   D
1301  GCTTGTTCAC TTGTGTATAT TCCTATGGTA AAGAGATTGT GAAATTTGAT
      CGAACAAGTG AACACATATA AGGATACCAT TTCTCTAACA CTTTAAACTA

+1    E   D   G   I   Q   L   N   Q   D   R   E   F   I   P   G   F   W
1351  GAAGACGGTA TTCAGTTGAA TCAAGACAGA GAATTTATAC CGGGATTTTG
      CTTCTGCCAT AAGTCAACTT AGTTCTGTCT CTTAAATATG GCCCTAAAAC
```

FIG. 2G

```
+1        K  F  F  F  S  T  F  G  D  Q  S  E  G  G  L  S
1401      GAAGTTCTTC TTCAGTACAT TTGGGGATCA AGTGAAGGT GGTCTTAGTG
          CTTCAAGAAG AAGTCATGTA AACCCCTAGT TTCACTTCCA CCAGAATCAC

+1        A  A  F  K  G  V  T  I  K  Q  I  L  Y  E  S  S  P
1451      CTGCTTTCAA AGGTGTCACC ATTAAACAAA TACTTTACGA GTCAAGCCCC
          GACGAAAGTT TCCACAGTGG TAATTTGTTT ATGAAATGCT CAGTTCGGGG

+1        D  S  V  K  K  E  Q  D  A  S  K  V  N  K  L  K  V
1501      GATAGTGTTA AAAAGGAACA AGATGCTAGT AAAGTTAATA AACTGAAAGT
          CTATCACAAT TTTTCCTTGT TCTACGATCA TTTCAATTAT TTGACTTTCA

+1        K  L  V  L  L  W  E  F  A  K         V  S  E  C  K  D
1551      CAAATTGGTT TTACTTTGGG AATTTGCTAA AGTGAGTGAA TGCAAAGATG
          GTTTAACCAA AATGAAACCC TTAAACGATT TCACTCACTT ACGTTTCTAC
```

FIG. 2H

```
     +1  A  L  T  T  T  T  K  L  V  L  P  P  R  A  L  A  S
         ----------------------------------------]---------
   1601  CTTGACTAC TACTACAAAG TTGGTGTTAC CACCACGAGC ACTGGCTTCA
         GAAACTGATG ATGATGTTTC AACCACAATG GTGGTGCTCG TGACCGAAGT

+1  S  S  S  K  T  T  E  E  V  F  E  Y  S  E  P  A  L  N
         ----------]------------------------------]----------
   1651  AGCTCAAAGA CCACTGAAGA AGTGTTTGAA TACTCAGAAC CAGCATTAAA
         TCGAGTTTCT GGTGACTTCT TCACAAACTT ATGAGTCTTG GTCGTAATTT

+1  S  I  G  G  T  P  T  D  T  T  S  P  N  M  D  L
         -------------------------------------]----------
   1701  CTCAATTGGT GGTACCCCAA CGGACACTAC TAGTCCTAAT ATGGATTTGA
         GAGTTAACCA CCATGGGGTT GCCTGTGATG ATCAGGATTA TACCTAAACT

+1  N  N  Q  N  L  S  A  A  A  T  S  I  P  G  I  R  D
         ------------------------------------------------
   1751  ATAATCAGAA CTTGAGTGCA GCAGCAACTT CAATTCCTGG TATACGAGAC
         TATTAGTCTT GAACTCACGT CGTCGTTGAA GTTAAGGACC ATATGCTCTG
```

FIG. 21

```
+1    T   I   H   S   A   S   M   P   D   I   N   E   L   P   S   S   A
      ------------------------------------------------------------------
1801  ACCATTCATT CAGCATCAAT GCCAGATATC AATGAATTGC CATCTTCAGC
      TGGTAAGTAA GTCGTAGTTA CGGTCTATAG TTACTTAACG GTAGAAGTCG

+1    K   P   Q   V   R   L   Q   K   T   F   Q   S   M   Q   H   L
      ------------------------------------------------------------------
1851  TAAACCACAA GTAAGGTTAC AAAAGACTTT CCAATCGATG CAACACTTGC
      ATTTGGTGTT CATTCCAATG TTTTCTGAAA GGTTAGCTAC GTTGTGAACG

+1    Q   P   H   Q   M   W   Q   Q   Q   Q   Q   Q   P   L   Q   G
      ------------------------------------------------------------------
1901  AACCACACCA AATGTGGCAA CAACAACAAC AACAACAGCC ACTGCAAGGT
      TTGGTGTGGT TTACACCGTT GTTGTTGTTG TTGTTGTCGG TGACGTTCCA

+1    A   Y   T   S   S   V   A   S   Q   L   L   N   T   S   L   S   S
      ------------------------------------------------------------------
1951  GCATATACCA GCTCAGTAGC TTCACAACTG CTCAATACTT CATTATCATC
      CGTATATGGT CGAGTCATCG AAGTGTTGAC GAGTTATGAA GTAATAGTAG
```

FIG. 2J

```
+1       P   Y   A   Q   Y   G   M   P   L   P   Q   Q   T   I   G   T
2001    ACCTTATGCT CAATATGGCA TGCCACTACC ACAACAAACA ATAGGCACTT
        TGGAATACGA GTTATACCGT ACGGTGATGG TGTTGTTTGT TATCCGTGAA

+1       F   V   P   P   T   S   Q   T   F   G   V   S   Y   T   H   N   S
2051    TTGTTCCACC TACTTCACAA ACATTGGGTG TTTCCTACAC GCATAATAGC
        AACAAGGTGG ATGAAGTGTT TGTAAACCAC AAAGGATGTG CGTATTATCG

+1       Q   H   P   S   A   N   M   D   L   M   M   L   S   S   M   N   T
2101    CAACACCCTT CAGCTAATAT GGATCTTATG ATGCTTTCTT CTATGAATAC
        GTTGTGGGAA GTCGATTATA CCTAGAATAC TACGAAAGAA GATACTTATG

+1       G   Y   G   N   I   T   N   N   Q   D   Y   Q   F   G   N   I
2151    CGGATATGGA AATATCACGA ATAATCAAGA TTATCAATTT GGTAATATAG
        GCCTATACCT TTATAGTGCT TATTAGTTCT AATAGTTAAA CCATTATATC
```

FIG. 2K

+1 G Y T E G F T S E F
   ------------------->
2201 GATACACAGA AGGATTTACT AGTGAGTTTT AG
     CTATGTGTCT TCCTAAATGA TCACTCAAAA TC

FIG. 2L

CRV4 ORF

|   | FIG. 3A |
|---|---|
|   | FIG. 3B |
|   | FIG. 3C |
|   | FIG. 3D |
|   | FIG. 3E |
|   | FIG. 3F |
|   | FIG. 3G |
|   | FIG. 3H |

FIG. 3

```
+1     M   A   K   K   L   N   S   T   I   K   R   S   R   T   R   S
 1    ATGGCAAAGA AGAAACTAAA TTCAACAATA AAGGCAGCC GGACACGTTC
      TACCGTTTCT TCTTTGATTT AAGTTGTTAT TTCCGCGTCGG CCTGTGCAAG

+1     G   C   V   T   C   R   D   R   H   I   K   C   D   E   Q   Q
51    TGGTTGCGTT ACCTGTCGAG ATAGACATAT AAAATGCGAT GAACAACAAC
      ACCAACGCAA TGGACAGCTC TATCTGTATA TTTTACGCTA CTTGTTGTTG

+1     P   V   C   K   N   C   Q   K   S   N   R   K   C   Y   R   G   I
101   CTGTTTGCAA AAACTGTCAA AAATCAAATC GGAAATGTTA TCGAGGAATA
      GACAAACGTT TTTGACAGTT TTTAGTTTAG CCTTTACAAT AGCTCCTTAT

+1     R   L   N   F   T   Q   Y   T   F   Y   N   P   D   D   N   K   P
151   AGGTTAAACT TTACACAATA TACTTTTTAC AACCCTGATG ATAATAAGCC
      TCCAATTTGA AATGTGTTAT ATGAAAAATG TTGGGACTAC TATTATTCGG

+1     K   E   L   Q   Q   N   E   Q   P   N   S   S   H   Y   A   F
201   AAAAGAATTG CAACAAAATG AACAGCCAAA TAGTAGTCAT TATGCATTTC
      TTTTCTTAAC GTTGTTTTAC TTGTCGGTTT ATCATCAGTA ATACGTAAAG
```

FIG. 3A

```
+1   P   N   L   E   P   N   P   V   S   Q   K   H   R   I   L   D   Q
251  CCAATCTAGA GCCAAATCCA GTATCACAAA AACATAGGAT ATTAGACCAA
     GGTTAGATCT CGGTTTAGGT CATAGTGTTT TTGTATCCTA TAATCTGGTT

+1   S   I   T   I   A   S   L   Y   D   D   L   K   K   Y   K   P   Y
301  TCAATAACCA TTGCCTCATT ATATGATGAT TTGAAAAAGT ATAAGCCATA
     AGTTATTGGT AACGGAGTAA TATACTACTA AACTTTTTCA TATTCGGTAT

+1   I   H   L   H   T   P   E   D   L   R   E   S   D   L   Q   F
351  TATTCATTTA CATACACCAG AAGATTTAAG GGAGTCGGAC TTACAATTCC
     ATAAGTAAAT GTATGTGGTC TTCTAAATTC CCTCAGCCTG AATGTTAAGG

+1   Q   E   D   T   Y   N   S   Y   I   S   T   S   A   I   N   L   R
401  AAGAAGACAC ATACAATTCG TATATATCCA CATCTGCAAT AAATTTACGG
     TTCTTCTGTG TATGTTAAGC ATATATAGGT GTAGACGTTA TTTAAATGCC

+1   G   K   K   L   T   K   R   D   P   G   L   S   T   S   L   S   V
451  GGAAAAAAAT TGACTAAAAG AGATCCGGGG TTGTCTACTT CATTGTCAGT
     CCTTTTTTTA ACTGATTTTC TCTAGGCCCC AACAGATGAA GTAACAGTCA
```

FIG. 3B

```
     I   N   P   T   L   E   S   E   I   K   P   N   P   V   I   L
+1
501  TATTAATCCC ACATTGGAAT CTGAAATTAA ACCGAACCCG GTGATATTGA
     ATAATTAGGG TGTAACCTTA GACTTTAATT TGGCTTGGGC CACTATAACT

N   Q   L   S   F   H   P   P   P   N   L   N   T   G   V   L   Y
+1
551  ATCAATTGAG TTTCCACCCC CCACCAAATC TTAATACTGG AGTTTTGTAT
     TAGTTAACTC AAAGGTGGGG GGTGGTTTAG AATTATGACC TCAAAACATA

P   P   T   A   A   T   A   A   T   T   T   T   S   S   P   T   N   H
+1
601  CCACCAACCG CAACAGCAGC AACAACAACA ACATCAAGTC CTACTAATCA
     GGTGGTTGGC GTTGTCGTCG TTGTTGTTGT TGTAGTTCAG GATGATTAGT

H   L   H   P   Y   F   V   S   L   I   P   N   P   Q   H   H
+1
651  TCATTTACAT CCCTATTTTG TCAGTCTGAT ACCAAATCCA CAACATCATC
     AGTAAATGTA GGGATAAAAC AGTCAGACTA TGGTTTAGGT GTTGTAGTAG

P   M   L   D   T   S   Q   H   Q   E   T   T   S   T   D   P   N
+1
701  CAATGCTAGA CACTTCTCAA CATCAAGAGA CTACATCAAC AGACCCTAAT
     GTTACGATCT GTGAAGAGTT GTAGTTCTCT GATGTAGTTG TCTGGGATTA
```

FIG. 3C

```
     Q  F  D  Y  S  H  L     S  M  P     Q  S  T  P     L  L  M
+1   CAATTCGATT ATTCCCATCT ATCAATGCCT CAATCCACAC CCTTGCTAAT
751  GTTAAGCTAA TAAGGGTAGA TAGTTACGGA GTTAGGTGTG GGAACGATTA

K  Y  D     I  T  T  Y  V  R  L     I  E  T     E  K  Y
+1   GAAATACGAT ATCACCACCT ATGTAAGGTT AATTGAAACA GAAAAGTATT
801  CTTTATGCTA TAGTGGTGGA TACATTCCAA TTAACTTTGT CTTTTCATAA

Y  M  L  L     D  L  A     N  E  L  D  I  W  K  K  I  I
+1   ACATGCTATT GGATCTTGCC AATGAATTAG ATATTTGGAA AAAAATTATA
851  TGTACGATAA CCTAGAACGG TTACTTAATC TATAAACCTT TTTTTAATAT

P  S  L  C     L  Q  I     S  E  N     D  S  F  L  L  D  C
+1   CCGTCATTGT GTTGCAAAT TCCGAGAAT GATTCATTCT TGTTAGATTG
901  GGCAGTAACA CAAACGTTTA AGGCTCTTA CTAAGTAAGA ACAATCTAAC

L  M  S     C  S  R  N     T  S  V     N  L  L     D  L  T
+1   TTTGATGAGC TGTTCTCGTA ATACATCTGT TAACCTTTTG GACTTGACTA
951  AAACTACTCG ACAAGAGCAT TATGTAGACA ATTGGAAAAC CTGAACTGAT
```

FIG. 3D

```
      +1   N   E   Q   L   N   K   W   S   Q   L   K   N   A   P   V   I   S
    1001   ATGAACAATT GAATAAGTGG TCGCAATTGA AAAATGCTCC CGTGATATCA
           TACTTGTTAA CTTATTCACC AGCGTTAACT TTTTACGAGG GCACTATAGT

+1   E   R   I   Q   Q   F   E   H   I   L   I   S   I   V   L   I   L
    1051   GAAAGAATTC AACAATTTGA ACATATACTA ATAAGTATTG TATTAATTTT
           CTTTCTTAAG TTGTTAAACT TGTATATGAT TATTCATAAC ATAATTAAAA

+1   L   G   L   Y   L   N   T   T   K   V   R   L   T   D   Y   H
    1101   ACTTGGATTA TATTTGAATA CGACTAAAGT TCGACTAACT GATTATCATA
           TGAACCTAAT ATAAACTTAT GCTGATTTCA AGCTGATTGA CTAATAGTAT

+1   K   V   I   F   N   N   Q   A   K   L   F   S   H   V   L   R   K
    1151   AGGTGATTTT CAATAATCAA GCCAAATTGT TTTCCCACGT ATTGCGCAAG
           TCCACTAAAA GTTATTAGTT CGGTTTAACA AAAGGGTGCA TAACGCGTTC

+1   I   H   T   F   F   I   T   S   N   K   P   N   S   A   V   L   T   N
    1201   ATCCATACAT TTATCACATC AAATAAACCC AATTCGGCAG TATTGACAAA
           TAGGTATGTA AATAGTGTAG TTTATTTGGG TTAAGCCGTC ATAACTGTTT
```

FIG. 3E

```
      A   I   Q   S   I   T   M   L   K   F   F   I   D   K   N   Y
+1   TGCCATTCAA TCAATTACTA TGCTCAAATT TTTCATAGAT AAAAATTATG
1251 ACGGTAAGTT AGTTAATGAT ACGAGTTTAA AAAGTATCTA TTTTTAATAC

D   F   S   Y   E   F   K   N   I   Q   K   G   R   V   T   D   T
+1   ACTTCTCATA TGAATTTAAA AATATCCAGA AGGGAAGAGT TACTGATACA
1301 TGAAGAGTAT ACTTAAATTT TTATAGGTCT TCCCTTCTCA ATGACTATGT

L   E   E   I   T   Y   S   N   S   N   L   Y   S   N   P   D   I
+1   CTGGAGGAAA TCACGTATTC TAATTCGAAT TTATATTCCA ACCCGGATAT
1351 GACCTCCTTT AGTGCATAAG ATTAAGCTTA AATATAAGGT TGGGCCTATA

S   Y   I   S   T   F   N   E   Y   E   I   I   Y   L   N   N
+1   ATCCTATATT TCTACATTCA ACGAATACGA GATTATCTAC TTGAATAATT
1401 TAGGATATAA AGATGTAAGT TGCTTATGCT CTAATAGATG AACTTATTAA

S   Y   Q   N   L   V   H   V   D   Q   S   N   S   M   L   M   G
+1   CGTATCAGAA TCTTGTTCAC GTTGATCAAA GCAATAGTAT GCTGATGGGC
1451 GCATAGTCTT AGAACAAGTG CAACTAGTTT CGTTATCATA CGACTACCCG
```

FIG. 3F

```
      E  S  Q  L     Y  K  D     L  L  W     Y  L  M  K     V  D  F
+1
1501  GAATCTCAAT TATACAAAGA TCTATTGTGG TATTTGATGA AAGTTGATTT
      CTTAGAGTTA ATATGTTTCT AGATAACACC ATAAACTACT TTCAACTAAA

V  I  N     Y  P  E  A     A  N  N     L  V  L     D  H  N
+1
1551  TGTCATTAAT TATCCAGAAG CTGCCAACAA TTGGTTCTT GATCATAATG
      ACAGTAATTA ATAGGTCTTC GACGGTTGTT AACCAAGAA CTAGTATTAC

V  V  Y  Q     Q  I  T     N  A  S  T     D  L  S     F  S  N
+1
1601  TTGTTTATCA ACAAATTACT AATGCATCGA CTGATTGAG TTTCAGTAAT
      AACAAATAGT TGTTTAATGA TTACGTAGCT GACTAAACTC AAAGTCATTA

N  L  N  Y     L  N  P     R  S  Y     A  N  Y  F     L  K  E
+1
1651  AACTTGAATT ATTGAACCC AAGATCATAT GCAAATTATT TTTGAAAGA
      TTGAACTTAA TAAACTTGGG TTCTAGTATA CGTTTAATAA AAAACTTTCT

F  I  I     K  V  L  S     M  G  S     N  A  I     I  E  D
+1
1701  ATTTATTATC AAAGTATTGA GTATGGGTAG CAATGCCATC ATTGAAGATG
      TAAATAATAG TTTCATAACT CATACCCATC GTTACGGTAG TAACTTCTAC
```

FIG. 3G

```
+1   A  N  N  R   I  N  T   L  F  N  F   I  D  Q   S  Y  M
1751 CCAATAATCG AATAAATACT CTATTTAATT TTATTGATCA AAGCTATATG
     GGTTATTAGC TTATTTATGA GATAAATTAA AATAACTAGT TTCGATATAC

+1   D  P  E  L   K  S  Q   F  H  H   C  F  T  W   T  V  R
1801 GACCCAGAAC TAAAATCACA ATTTCATCAT TGCTTTACCT GGACTGTACG
     CTGGGTCTTG ATTTTAGTGT TAAAGTAGTA ACGAAATGGA CCTGACATGC

+1   Y  I  H   P  V  S  D
1851 CTACATTCAC CCAGTAAGTG AT
     GATGTAAGTG GGTCATTCAC TA
```

FIG. 3H

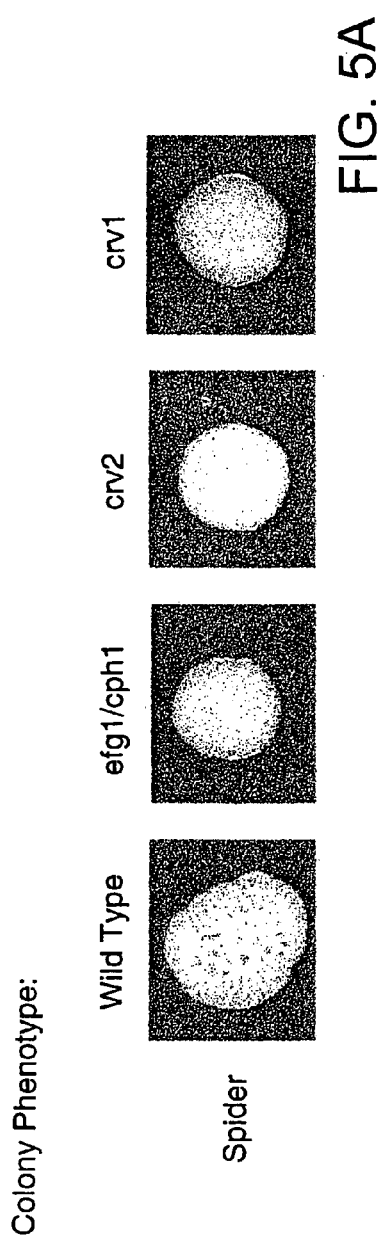
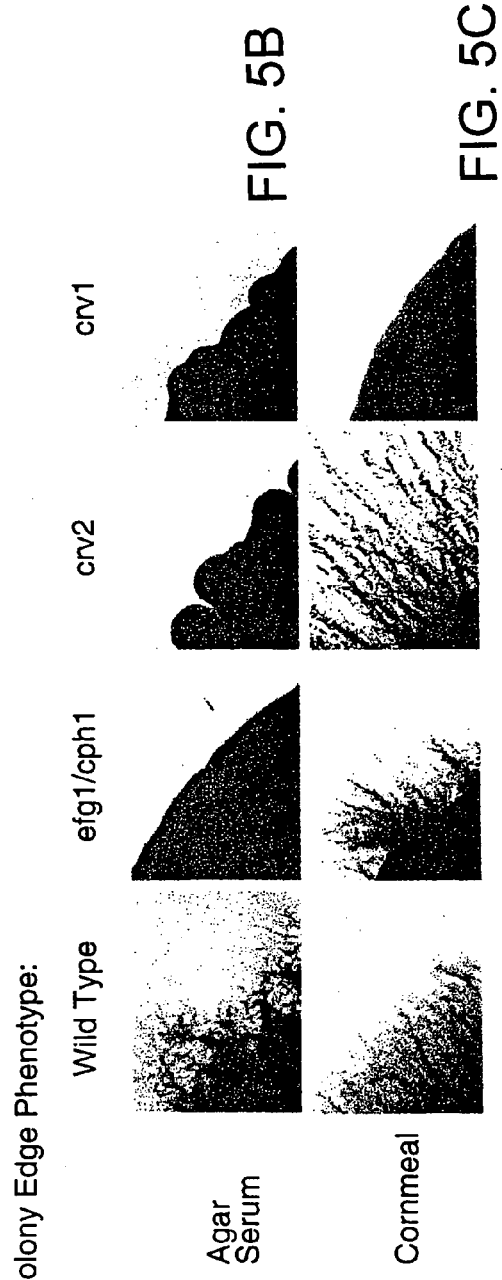

USE OF SUBLETHAL CONCENTRATIONS OF ANTI-INVASIN COMPOUNDS TO THERAPEUTICALLY OR PROPHYLACTICALLY TREAT FUNGAL INFECTIONS

This application is a continuation of and claims priority under 35 USC §119(e) to U.S. patent application Ser. No. 09/649,711, filed on Aug. 25, 2000 now abandoned, the entire contents of which are hereby incorporated by reference.

BACKGROUND OF THE INVENTION

1. Field of the Invention

The invention relates to the therapeutic or prophylactic treatment of fungal infections.

2. Summary of the Related Art

Fungal infections have become a serious health concern, especially in immunocompromised patients. Ha and White, Antimicrobial Agents and Chemotherapy 43: 763-768(1999) teaches that Candidiasis, which is caused by the pathogenic yeast *Candida albicans*, is the most frequent fungal infection associated with AIDS and other immunocompromised states. Weig et al., Trends in Microbiology 6: 468-470(1998) discloses that the frequency of *Candida* infections has increased in recent years and has been accompanied by a significant rise in morbidity and mortality. Many of these infections take place in the hospital setting. Baillie and Douglas, Methods in Enzymology 310: 644-656(1999) teaches that a majority of nosocomial septicemias caused by *Candida* species derive from biofilm formation on catheters and shunts.

Recently, there has been great interest in identifying genes that may be implicated as important virulence factors in these infections. Calera et al, Infection and Immunity 68: 518-525(2000) discloses that the SSK1 response regulator gene from *C. albicans* is essential for normal hyphal development and virulence. Alex et al., Proc. Natl. Acad. Sci. USA 95: 7069-7073(1998) teaches that COS1, a two-component histidine kinase, is required for normal hyphal growth of *C. albicans*, and may play a role in virulence properties of the organism. Alonso-Monge et al., J. Bacteriology 181: 3058-3068(1999) teaches that deletion of the *C. albicans* gene encoding the mitogen-activated protein kinase HOG1 causes derepression in serum induced hyphal formation and a dramatic increase in the survival time of systemically infected mice. Csank et al., Infection and Immunity 66: 2713-2721(1998) discloses that disruption of the *C. albicans* mitogen activated protein kinase CEK1 adversely affects the growth of serum induced mycelial colonies and attenuates virulence in a mouse model for systemic candidiasis. These and other studies have suggested that hyphal growth may be an important virulence factor in *C. albicans*. Lo et al., Cell 90: 939-949 (1997) teaches that nonfilamentous *C. albicans* mutants are avirulent. However, all of these mutants have other phenotypic changes, and at least some of them retain some virulence. Thus, it is not entirely clear that the virulence is being attenuated solely through blocking of germ tube formation.

The exact mechanism by which hyphal growth acts as a virulence factor is also not known with certainty. Kretschmar et al., Infection and Immunity 67: 6637-6642 (1999) teaches that there is a correlation between germ tube length and organ invasion in *C. albicans* clinical isolates. Van't Wout et al., J. Antimicrob. Chemother. 25: 803-811 (1990) discloses that *C. albicans* may resist intracellular killing by macrophages through the formation of germ tubes.

A variety of antifungal antibiotics have been developed, some of which also affect hyphal growth. Bremm et al., Candida and Candidamycosis (E. Tumbay, Ed.), Plenum Press, New York (1991) teaches that azole compounds have an influence on fungal adhesion. Brenciaglia et al., Chemioterapia 5: 200-203 (1986) teaches that amphotericin B interferes with *C. albicans* adherence in vitro at sub-minimum inhibitory concentrations (MIC), but that 5-fluorocytosine, nystatin, miconazole and ketoconazole interfere with adherence only at concentrations above MIC values. Amphotericin B and the azoles have become a first-line treatment for *Candida* infections. Martin, J. Antimicrob. Chemother 44: 429-437 (1999) teaches that fluconazole is preferably administered at 300-400 mg/day, depending on the localization of the infection, and that higher doses can be used successfully.

There is a need for even less toxic treatment regimens than those presently available. Tamburini et al., U.S. Pat. No. 5,833,946 teaches that there is a need for effective anti-*Candida* agents having fewer toxicological problems than amphotericin B, and which by virtue of their lower toxicities can be administered to high risk patients either prophylactically or at the earliest signs of infection, without the need for a firm diagnosis. Philpott-Howard et al., J. Antimicrob. Chemother. 31: 973-984 (1993) discloses that over 5% of patients treated with fluconazole had adverse reactions, possibly related to the treatment, about half of which necessitated discontinuation of therapy.

For nearly two decades, scientists have talked about the possibility of using sub-lethal (to the fungus) concentrations of agents that inhibit hyphal growth as a therapeutic treatment for fungal infections. Plempel and Berg, Dermatologica 169: 11-18 (1984) discloses that when *C. albicans* cells are pretreated with sub-inhibitory concentrations of azole compounds and injected intravenously in mice, the resultant infections are of reduced severity in comparison to controls. Haller, Am. J. Obstet. Gynecol. 152: 939-944 (1985) discloses that azole compounds inhibit mycelial growth in vitro at even 1% of MIC. Nugent and Couchot, J. Infect. Dis. 154: teaches that sub-lethal doses of amphotericin B inhibit *C. albicans* germ tube formation and adherence in vitro. Mehentee and Hay, J. Antimicrob. Chemother. 25: 111-119 (1990) discloses that sub-inhibitory concentrations of amphotericin B, ketoconazole and itraconazole significantly reduce the adherence of *C. albicans* to murine gastrointestinal mucosal surfaces in vitro. Ghannoum et al., Antimicrob. Agents Chemother. 36: 2239-2244 (1992) teaches that subinhibitory concentrations of fluconazole and amphotericin B block *C. albicans* ability to adhere to and injure human umbilical vein endothelial cells in vitro. Braga et al., Arzneimittelforschung 42: 1368-1371 (1992) teaches that sub-inhibitory concentrations of ciclopirox causes a significant reduction in *C. albicans* adherence to human buccal cells and human vaginal cells in vitro. Braga et al., Chemotherapy 42: 259-265 (1996) discloses that sub-inhibitory concentrations of rilopirox, nystatin and fluconazole interfere with *C. albicans* adherence to human vaginal cells in vitro. Ellepola and Samaranayake, Arch. Oral. Biol. 43: 999-1007 (1998) suggests that sub-therapeutic doses of antifungals may modulate oral candidal colonization, based upon in vitro studies. Ellepola and Samaranayake, J. Oral Pathol. Med. 27: 325-332 (1998) teaches that sub-lethal concentrations of nystatin, 5-fluorocytosine, ketoconazole and fluconazole reduces binding of *C. albicans* to buccal epithelial cells in vitro. Ellepola and Samaranayake, J. Oral Pathol. Med. 27: 213-219 (1998) discloses that sub-lethal concentrations of nystatin, amphotericin B, 5-fluorocytosine, ketoconazole and fluconazole inhibit germ tube formation by *C. albicans* in vitro. Ha and White, Antimicrobial Agents and Chemotherapy 43: 763-768 (1999) teaches that as little as 0.1 μg/ml fluconazole reduces hyphal formation in a susceptible isolate of *C. albicans* in vitro.

Recently, considerable doubt has been cast as to whether fungistatic agents, such as the azoles, can actually inhibit morphogenic transformation at sub-MIC levels. Hawser et al., J. Antimicrob. Chemother. 38: 579-587 (1996) teaches that when NCCLS guidelines are used in the study, ketoconazole can only block the transformation at very high concentrations. Hawser and Islam, J. Antimicrob. Chemother. 43: 411-413 (1999) teaches that antifungal agents that are more fungicidal, such as amphotericin B and the candins are able to inhibit morphogenic transformation at sub-MIC levels, whereas fungistatic agents, such as the azoles, are not.

Despite all of these in vitro studies over many years, no one has succeeded at therapeutically or prophylactically treating fungal infections using sub-lethal concentrations of an anti-invasin compound. There is, therefore, a need for new methods for therapeutically or prophylactically treating fungal infections using sub-lethal concentrations of an anti-invasin compound.

BRIEF SUMMARY OF THE INVENTION

The invention provides new methods for therapeutically or prophylactically treating fungal infections using sub-lethal concentrations of an anti-invasin compound. The methods according to the invention have fewer toxicology problems than existing methods, and thus can be used prophylactically, as well as for early treatment for high-risk patients without a firm diagnosis. The methods according to the invention can also be used to treat an established fungal infection.

In a first aspect, the invention provides methods for therapeutically treating a patient having a fungal infection. The methods according to this aspect of the invention comprise administering to the patient a sub-inhibitory concentration of an anti-invasin compound. In preferred embodiments of this aspect of the invention, the fungal infection is candidiasis. In preferred embodiments of this aspect of the invention, the anti-invasin compound is selected from the group consisting of candins, polyenes, cyclic peptide inhibitors of β-glucan synthetase, 5-fluorocytosine, and azole compounds.

In a second aspect, the invention provides methods for prophylactically treating a patient to prevent a fungal infection. The methods according to this aspect of the invention comprise administering to a patient at risk of developing a fungal infection a sub-inhibitory concentration of an anti-invasin compound. In preferred embodiments of this aspect of the invention, the fungal infection is candidiasis. In preferred embodiments of this aspect of the invention, the anti-invasin compound is selected from the group consisting of candins, polyenes, cyclic peptide inhibitors of β-glucan synthetase, 5-fluorocytosine, and azole compounds.

In a third aspect, the invention provides methods for preventing or eliminating formation of fungal biofilms in a medical device. The methods according to this aspect of the invention comprise providing to the medical device a sub-inhibitory concentration of an anti-invasin compound. In preferred embodiments of this aspect of the invention, the biofilm is a *Candida* fungus biofilm. In preferred embodiments of this aspect of the invention, the anti-invasin compound is selected from the group consisting of candins, polyenes, cyclic peptide inhibitors of β-glucan synthetase, 5-fluorocytosine, and azole compounds In a fourth aspect, the invention provides methods for therapeutically treating a patient having a fungal infection. The methods according to this aspect of the invention comprise administering to the patient an inhibitor of CRV-1.

In a fifth aspect, the invention provides methods for prophylactically treating a patient to prevent a fungal infection. The methods according to this aspect of the invention comprise administering to a patient at risk of developing a fungal infection an inhibitor of CRV-1.

In a sixth aspect, the invention provides methods for avoiding or eliminating formation of fungal biofilms in a medical device. The methods according to this aspect of the invention comprise providing to the medical device an inhibitor of CRV-1.

In a seventh aspect, the invention provides methods for therapeutically treating a patient having a fungal infection. The methods according to this aspect of the invention comprise administering to the patient an inhibitor of CRV-2.

In an eighth aspect, the invention provides methods for prophylactically treating a patient to prevent a fungal infection. The methods according to this aspect of the invention comprise administering to a patient at risk of developing a fungal infection an inhibitor of CRV-2.

In a ninth aspect, the invention provides methods for avoiding or eliminating formation of fungal biofilms in a medical device. The methods according to this aspect of the invention comprise providing to the medical device an inhibitor of CRV-2.

In a tenth aspect, the invention provides methods for therapeutically treating a patient having a fungal infection. The methods according to this aspect of the invention comprise administering to the patient an inhibitor of CRV-4.

In an eleventh aspect, the invention provides methods for prophylactically treating a patient to prevent a fungal infection. The methods according to this aspect of the invention comprise administering to a patient at risk of developing a fungal infection an inhibitor of CRV-4.

In a twelfth aspect, the invention provides methods for avoiding or eliminating formation of fungal biofilms in a medical device. The methods according to this aspect of the invention comprise providing to the medical device an inhibitor of CRV-4.

In a thirteenth aspect, the invention provides novel genes that are useful for regulating hyphal growth of fungi. In preferred embodiments, the novel genes are selected from the group consisting of CRV-1, CRV-2 and CRV-4, and variants thereof.

In a fourteenth aspect, the invention provides purified polypeptides and peptidomimetics that are useful for regulating hyphal growth of fungi. In preferred embodiments, the novel polypeptides are selected from the group consisting of CRV-1, CRV-2 and CRV-4, and variants thereof.

In a fifteenth aspect, the invention provides methods for identifying binding agents that are useful for regulating hyphal growth of fungi. The methods according to this aspect of the invention comprise treating a first wild-type fungus with a proposed binding agent to obtain a first result, treating a second mutant fungus with the same proposed binding agent to obtain a second result, and comparing the first and second results, wherein the mutant fungus is selected from the group consisting of a null mutant for CRV-1, a null mutant for CRV-2 and a null mutant for CRV-4. In certain preferred embodiments, the method is carried out in vitro. In certain other preferred embodiments, the method is carried out in vivo.

In a sixteenth aspect, the invention provides another method for identifying binding agents that are useful for regulating hyphal growth. In the method according to this aspect of the invention, a purified polypeptide according to the fourteenth aspect of the invention is contacted with a molecule that is a potential binding agent under conditions under which such binding is detectable.

In a seventeenth aspect, the invention provides a binding agent specific for a protein selected from the group consisting of CRV-1, CRV-2 and CRV-4.

BRIEF DESCRIPTION OF THE DRAWINGS

FIGS. 1A-1M shows the nucleotide sequence (SEQ ID NO:1) and predicted amino acid sequence (SEQ ID NO:2) for CRV-1. The complementary strand is also shown (SEQ ID NO:19.

FIGS. 2A-2L shows the nucleotide sequence (SEQ ID NO:3) and predicted amino acid sequence (SEQ ID NO:4) for CRV-2. The complementary strand is also shown (SEQ ID NO:20).

FIGS. 3A-3H shows the nucleotide sequence (SEQ ID NO:5) and predicted amino acid sequence (SEQ ID NO:6) for CRV-4. The complementary strand is also shown (SEQ ID NO:21.

FIGS. 5A-5D shows phenotypes of various strains of *C. albicans* under conditions favoring hyphal growth.

DETAILED DESCRIPTION OF THE PREFERRED EMBODIMENTS

Figure 4:
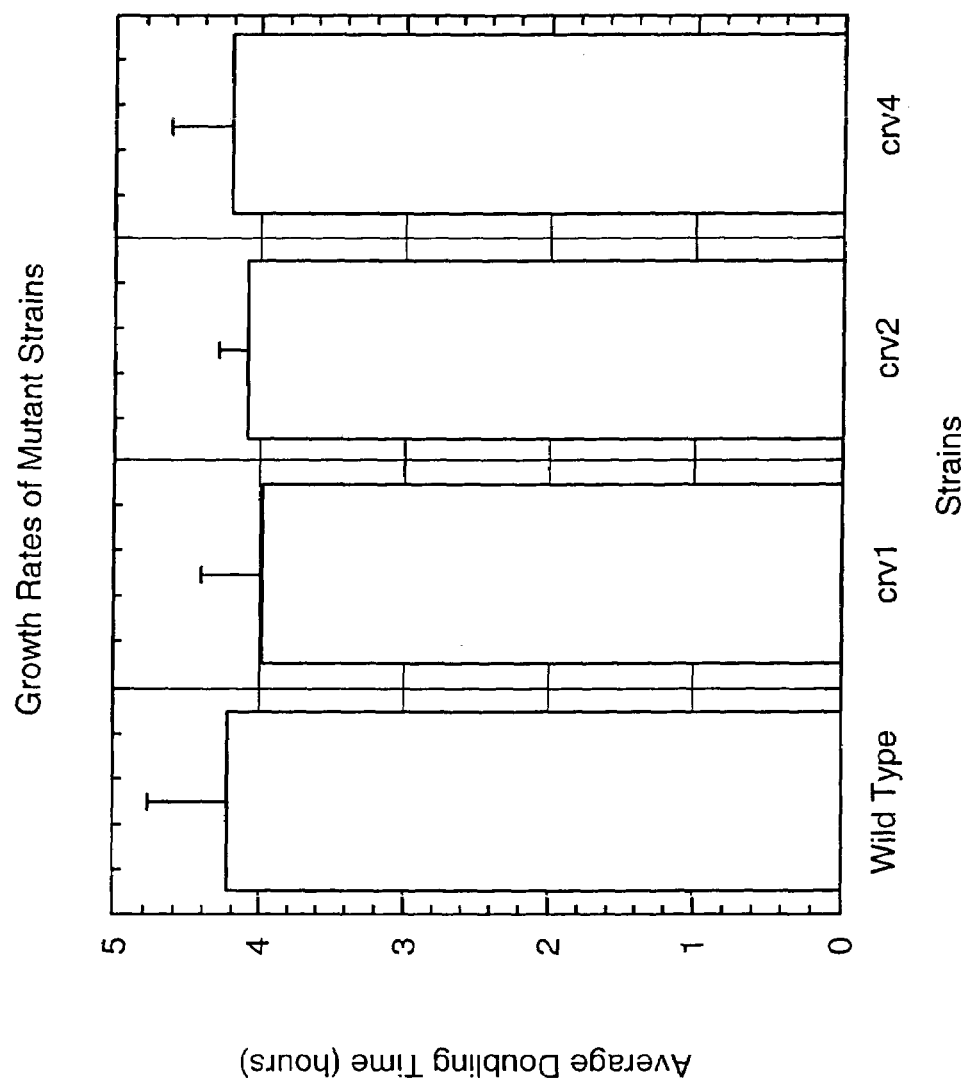
FIG. 4 shows growth rates for various strains of *C. albicans*.

The invention relates to the therapeutic or prophylactic treatment of fungal infections. The patents and publications cited herein reflect the level of knowledge in this field and are hereby incorporated by reference in their entirety. In the case of conflict between the teaching of a cited reference and the present specification, the latter shall prevail.

The invention provides new methods for therapeutically or prophylactically treating fungal infections using sub-lethal concentrations of an anti-invasin compound. The methods according to the invention have fewer toxicology problems than existing methods, and thus can be used prophylactically, as well as for early treatment for high-risk patients without a firm diagnosis. The methods according to the invention can also be used to treat an established fungal infection.

In a first aspect, the invention provides methods for therapeutically treating a patient having a fungal infection. The methods according to this aspect of the invention comprise administering to the patient a sub-inhibitory concentration of an anti-invasin compound. As used throughout this specification, the sub-inhibitory concentration is a therapeutically effective concentration. "Therapeutically effective" means having the ability to reduce or eliminate the clinically recognized signs and symptoms of fungal infection. In certain preferred embodiments of this aspect of the invention, the fungal infection is candidiasis. In preferred embodiments of this aspect of the invention, the anti-invasin compound is selected from the group consisting of candins, polyenes, cyclic peptide inhibitors of β-glucan synthetase, 5-fluorocytosine, and azole compounds. In certain particularly preferred embodiments, the anti-invasin compound is a fungistatic compound, including without limitation 5-fluorocytosine and azole compounds. As used herein, the term "sub-inhibitory concentration" means a concentration of the inhibitor that is lower than the minimum inhibitory concentration (MIC). See National Committee for Clinical Laboratory Standards, (1995) Reference Method for Broth dilution Antifungal Susceptibility Testing of Yeasts: Approved Standard M27-A. NCCLS, Villanova, Pa; ISBN 1-56238-186-5. Preferably, the sub-inhibitory concentration is less than one-half, more preferably less than one-fourth, even more preferably less than one-eighth, and most preferably less than one-sixteenth the MIC. The term "anti-invasin compound" means a compound that prevents the fungus from growing in a hyphal form under conditions that otherwise would lead to hyphal growth, e.g., neutral pH, serum, 37C. The term "azole compounds" includes any of the imidazole or triazole compounds in which the azole ring is N-linked to a short aliphatic chain in which the second carbon is linked to a halogenated phenyl group, including without limitation miconazole, ketoconazole, clotrimazole, bifonazole, R3783, fluconazole, terconazole, butoconazole, econazole, SCH39304, voriconazole, saperconazole, itraconazole, ICI 153066 and ICI 195739.

Such inhibitors of hyphal growth can be administered by conventional approaches, including, without limitation, orally, parenterally, transdermally, and transmucosally. The inhibitors may be formulated using any conventional formulation. See, e.g., AHFS Drug Information, 2000, First Edition, Amer Soc of Health System, ISBN 1585280046 (2000).

In a second aspect, the invention provides methods for prophylactically treating a patient to prevent a fungal infection. The methods according to this aspect of the invention comprise administering to a patient at risk of developing a fungal infection a sub-inhibitory concentration of an anti-invasin compound. In preferred embodiments of this aspect of the invention, the fungal infection is candidiasis. In preferred embodiments of this aspect of the invention, the anti-invasin compound is selected from the group consisting of candins, polyenes, cyclic peptide inhibitors of β-glucan synthetase, 5-fluorocytosine, and azole compounds. In certain particularly preferred embodiments, the anti-invasin compound is a fungistatic compound, including without limitation 5-fluorocytosine and azole compounds. The terms "sub-inhibitory concentration", "anti-invasin compound" and "azole compounds" are as defined previously.

Such inhibitors can be administered by conventional approaches, including, without limitation, orally, parenterally, transdermally, and transmucosally. The inhibitors may be formulated using any conventional formulation.

In a third aspect, the invention provides methods for preventing or eliminating formation of fungal biofilms in a medical device. The methods according to this aspect of the invention comprise providing to the medical device a sub-inhibitory concentration of an anti-invasin compound. In preferred embodiments of this aspect of the invention, the biofilm is a *Candida* fungus biofilm.

In preferred embodiments of this aspect of the invention, the anti-invasin compound is selected from the group consisting of candins, polyenes, cyclic peptide inhibitors of β-glucan synthetase, 5-fluorocytosine, and azole compounds. In certain particularly preferred embodiments, the anti-invasin compound is a fungistatic compound, including without limitation 5-fluorocytosine and azole compounds. The terms "sub-inhibitory concentration", "anti-invasin compound" and "azole compounds" are as defined previously. According to this aspect of the invention, a solution of the inhibitor can be in fluid communication with the interior of the medical device, or the anti-invasin compound can be incorporated into the material from which the medical device is made.

In a fourth aspect, the invention provides methods for therapeutically treating a patient having a fungal infection. The methods according to this aspect of the invention comprise administering to the patient an inhibitor of CRV-1 (See FIGS. 1A-1M). In all of the following aspects of the invention it is not a requirement that the dosage of inhibitor be sub-inhibitory, although in some cases it may be preferred. In cases where sub-inhibitory concentrations are preferred, the term "sub-inhibitory concentration" is as defined previously.

In certain embodiments, the inhibitor of CRV-1 is an inhibitor of gene expression of CRV-1 or of a gene that upregulates CRV-1 expression or that is required for CRV-1 expression, or an upregulator of a gene that down-regulates CRV-1. An "inhibitor of gene expression of CRV-1" is a molecule that directly or indirectly causes CRV-1 transcription and/or translation and/or gene product maturation to be reduced by at least two-fold, preferably at least five fold, and more preferably at least ten-fold, the level of such expression that would be present under similar growth conditions in the absence of the inhibitor of expression of the gene. "Similar growth conditions" means similar sources of nutrients such as carbon, nitrogen, and phosphate, as well as similar pH, partial oxygen pressure, temperature, concentration of drugs or other small molecules, and a similar substrate for growth, whether solid, semi-solid, or liquid.

In certain embodiments, the inhibitor of CRV-1 is a peptide or peptidomimetic inhibitor of gene expression. The term "peptide" means a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above. Peptides may be supplied exogenously, preferably on a scaffold to increase intracellular stability and to provide conformational constraint. A "scaffold" is a molecule, most frequently a small protein, from which a peptide is displayed; scaffolds are employed to optimize presentation, rigidity, conformational constraint, and potentially intracellular/extracellular localization. Preferred scaffolds include a catalytically inactive version of staphylococcal nuclease. Preferred peptides according to this aspect of the invention include, without limitation, those peptides disclosed in Norman et al., Science 285: 591-595 (1999). The peptides according to this aspect of the invention can then be used to design peptidomimetics using standard procedures. See e.g., Kazmierski, Peptidomimetics Protocols, Humana Press (1999).

In certain embodiments of the methods according to this aspect of the invention, the inhibitor is a small molecule inhibitor of gene expression. A "small molecule" is a compound with a preferable molecular weight below 1000 daltons.

In certain embodiments, the inhibitor interferes with the function of CRV-1 protein. "Interferes with the function of CRV-1 protein" means that one or more activity of CRV-1 protein is specifically reduced, preferably at least 2-fold, more preferably at least 5-fold, even more preferably at least 10-fold, and most preferably completely. This may be observed using an agar plate "agar invasion assay". "Specifically reduced" means that the activity of CRV-1 is reduced more than the activity of an unrelated protein, preferably at least 2-fold more, more preferably at least 5-fold more, and most preferably at least 10-fold more. An "unrelated protein" is a protein that is not regulated by CRV-1. In certain embodiments, such an inhibitor may be a peptide, as that term has been defined previously. In certain embodiments, such an inhibitor may be a small molecule, as that term has been defined previously.

Inhibitors of CRV-1 are preferably administered at a dosage that inhibits CRV-1 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In a fifth aspect, the invention provides methods for prophylactically treating a patient to prevent a fungal infection. The methods according to this aspect of the invention comprise administering to a patient at risk of developing a fungal infection an inhibitor of CRV-1. The term "inhibitor of CRV-1 " is as described in the fourth aspect of the invention. Inhibitors of CRV-1 are preferably administered at a dosage that inhibits CRV-1 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In a sixth aspect, the invention provides methods for avoiding or eliminating formation of fungal biofilms in a medical device. The methods according to this aspect of the invention comprise providing to the medical device an inhibitor of CRV-1. The term "inhibitor of CRV-1" is as described in the fourth aspect of the invention. Inhibitors of CRV-1 are preferably administered at a dosage that inhibits CRV-1 at least 2-fold, more preferably at least 5-fold, even more preferably at least 10-fold and most preferably completely. The inhibitor of CRV-1 can be in a solution in fluid communication with the interior of the medical device, or it can be incorporated into the material from which the medical device is made.

In a seventh aspect, the invention provides methods for therapeutically treating a patient having a fungal infection. The methods according to this aspect of the invention comprise administering to the patient an inhibitor of CRV-2.

In certain embodiments, the inhibitor of CRV-2 is an inhibitor of gene expression of CRV-2 or of a gene that upregulates CRV-2 expression or that is required for CRV-2 expression, or an upregulator of a gene that down-regulates CRV-2. An "inhibitor of gene expression of CRV-2" is a molecule that directly or indirectly causes CRV-2 transcription and/or translation and/or gene product maturation to be reduced by at least two-fold, preferably at least five fold, and more preferably at least ten-fold, the level of such expression that would be present under similar growth conditions in the absence of the inhibitor of expression of the gene. "Similar growth conditions" means similar sources of nutrients such as carbon, nitrogen, and phosphate, as well as similar pH, partial oxygen pressure, temperature, concentration of drugs or other small molecules, and a similar substrate for growth, whether solid, semi-solid, or liquid.

In certain embodiments of the methods according to this aspect of the invention, the inhibitor is a peptide inhibitor of gene expression. The term "peptide" is as described previously.

In certain embodiments of the methods according to this aspect of the invention, the inhibitor is a small molecule inhibitor of gene expression. The term "small molecule" is as defined previously.

In certain embodiments, the inhibitor interferes with the function of CRV-2 protein. "Interferes with the function of CRV-2 protein" means that one or more activity of CRV-2 protein is specifically reduced, preferably at least 2-fold, more preferably at least 5-fold, even more preferably at least 10-fold, and most preferably completely. "Specifically reduced" means that the activity of CRV-2 is reduced more than the activity of an unrelated protein, preferably at least 2-fold more, more preferably at least 5-fold more, and most preferably at least 10-fold more. An "unrelated protein" is a protein that is not regulated by CRV-2. In certain embodiments, such an inhibitor may be a peptide, as that term has been defined previously. In certain embodiments, such an inhibitor may be a small molecule, as that term has been defined previously.

Inhibitors of CRV-2 are preferably administered at a dosage that inhibits CRV-2 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In an eighth aspect, the invention provides methods for prophylactically treating a patient to prevent a fungal infection. The methods according to this aspect of the invention comprise administering to a patient at risk of developing a fungal infection an inhibitor of CRV-2. The term "inhibitor of CRV-2" is as described in the seventh aspect of the invention. Inhibitors of CRV-1 are preferably administered at a dosage that inhibits CRV-1 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In a ninth aspect, the invention provides methods for avoiding or eliminating formation of fungal biofilms in a medical device. The methods according to this aspect of the invention comprise providing to the medical device an inhibitor of CRV-2. The term "inhibitor of CRV-2" is as described in the seventh aspect of the invention. Inhibitors of CRV-2 are preferably administered at a dosage that inhibits CRV-2 at least 2-fold, more preferably at least 5-fold, even more preferably at least 10-fold and most preferably completely. The inhibitor of CRV-2 can be in a solution in fluid communication with the interior of the medical device, or it can be incorporated into the material from which the medical device is made.

In a tenth aspect, the invention provides methods for therapeutically treating a patient having a fungal infection. The methods according to this aspect of the invention comprise administering to the patient an inhibitor of CRV-4.

In certain embodiments, the inhibitor of CRV-4 is an inhibitor of gene expression of CRV-4 or of a gene that upregulates CRV-4 expression or that is required for CRV-4 expression, or an upregulator of a gene that down-regulates CRV-4. An "inhibitor of gene expression of CRV-4" is a molecule that directly or indirectly causes CRV-4 transcription and/or translation and/or gene product maturation to be reduced by at least two-fold, preferably at least five fold, and more preferably at least ten-fold, the level of such expression that would be present under similar growth conditions in the absence of the inhibitor of expression of the gene. "Similar growth conditions" means similar sources of nutrients such as carbon, nitrogen, and phosphate, as well as similar pH, partial oxygen pressure, temperature, concentration of drugs or other small molecules, and a similar substrate for growth, whether solid, semi-solid, or liquid.

In certain embodiments of the methods according to this aspect of the invention, the inhibitor is a peptide inhibitor of gene expression. The term "peptide" is as described previously.

In certain embodiments of the methods according to this aspect of the invention, inhibitor is a small molecule inhibitor of gene expression. The term "small molecule" is as defined previously.

In certain embodiments, the inhibitor interferes with the function of CRV-4 protein. "Interferes with the function of CRV-4 protein" means that one or more activity of CRV-4 protein is specifically reduced, preferably at least 2-fold, more preferably at least 5-fold, even more preferably at least 10-fold, and most preferably completely. "Specifically reduced" means that the activity of CRV-4 is reduced more than the activity of an unrelated protein, preferably at least 2-fold more, more preferably at least 5-fold more, and most preferably at least 10-fold more. An "unrelated protein" is a protein that is not regulated by CRV-4. In certain embodiments, such an inhibitor may be a peptide, as that term has been defined previously. In certain embodiments, such an inhibitor may be a small molecule, as that term has been defined previously.

Inhibitors of CRV-4 are preferably administered at a dosage that inhibits CRV-4 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In an eleventh aspect, the invention provides methods for prophylactically treating a patient to prevent a fungal infection. The methods according to this aspect of the invention comprise administering to a patient at risk of developing an inhibitor of CRV-4. The term "inhibitor of CRV-4" is as described in the tenth aspect of the invention. Inhibitors of CRV-4 are preferably administered at a dosage that inhibits CRV-4 at least 2-fold, more preferably at least 5-fold, even more preferably at least 10-fold and most preferably completely. Such inhibitors can be administered by conventional approaches, including, without limitation, orally, parenterally, transdermally, and transmucosally. The inhibitors may be formulated using any conventional formulation.

In a twelfth aspect, the invention provides methods for avoiding or eliminating formation of fungal biofilms in a medical device. The methods according to this aspect of the invention comprise providing to the medical device an inhibitor of CRV-4. The term "inhibitor of CRV-4" is as described in the tenth aspect of the invention. Inhibitors of CRV-4 are preferably administered at a dosage that inhibits CRV-4 at least 2-fold, more preferably at least 5-fold, even more preferably at least 10-fold and most preferably completely. The inhibitor of CRV-4 can be in a solution in fluid communication with the interior of the medical device, or it can be incorporated into the material from which the medical device is made.

In a thirteenth aspect, the invention provides novel genes that are useful for regulating hyphal growth of fungi. In preferred embodiments, the novel genes are selected from the group consisting of CRV-1 and CRV-1 variants, CRV-2 variants and CRV-4 variants. The gene CRV-1 has the nucleotide sequence shown in the sequence listing as SEQ. ID. NO: 1. A "variant" of CRV-1 is a nucleotide sequence having the sequence from positions SHOWN IN SEQ. ID. NO: 1 as 1877-2298, or a sequence 90% homologous thereto and having an overall homology to CRV-1 of at least 50%. The gene CRV-2 has the nucleotide sequence shown in the sequence listing as SEQ. ID. NO. 3. A "variant" of CRV-2 is a nucleotide sequence having at least 80%, but less than 100% homology to the TEA domain of CRv-2. The gene CRV-4 has the nucleotide sequence shown in the sequence listing as SEQ. ID. NO. 5. A "variant" of CRV-4 is a nucleotide sequence having at least 80%, but less than 100% homology to the TEA domain of CRV-4. The novel genes according to this aspect are recombinant or isolated. The algorithm used to define the % homology throughout this specification is disclosed in Altschul et al., Nucleic Acids Res. 25: 3389-3402 (1997). Variants also may be determined by their ability to hybridize with the claimed gene under medium stringency, or preferably high stringency conditions. "High and medium stringency conditions for nucleic acid hybridizations are described on pages 2.10.1-2.10.16 (see particularly 1.10.8-11) in Current protocols in molecular biology (Ausubel, F. M. et al., Eds., Vol 1. (1995). Generally, % homology is preferred over hybridization. "Isolated" means that the gene is free of other unrelated DNA. "Recombinant" means that the gene is covalently linked to other DNA, but that other DNA is not identical to the DNA to which the gene had been covalently linked in its native chromosomal locus. Genes according to this aspect of the invention are useful in regulating hyphal growth of fungi.

In a fourteenth aspect, the invention provides purified polypeptides that are useful for regulating hyphal growth of fungi. In preferred embodiments, the novel polypeptides are selected from the group consisting of CRV-1 and CRV-1 variants, CRV-2 variants and CRV-4 variants. The polypeptide CRV-1 has the amino acid sequence shown in the sequence listing as SEQ. ID. NO: 2. A "variant" of CRV-1 is a polypeptide sequence encoded by the sequence shown in SEQ. ID. NO: 1 as positions 1877-2298, or a sequence 90% homologous thereto and having an overall homology to CRV-1 of at least 50%. The polypeptide CRV-2 has the amino acid sequence shown in the sequence listing as SEQ. ID. NO:4. A "variant" of CRV-2 is a polypeptide sequence having at least 80%, but less than 100% homology to CRV-2. The polypeptide CRV-4 has the nucleotide sequence shown in the sequence listing as SEQ. IDL. NO: 5. A "variant" of CRV-4 is a nucleotide sequence having at least 70%, but less than 100% homology to CRV-4. A "purified" polypeptide is a protein preparation in which the polypeptide comprises at least 70% of the overall protein weight of the preparation, more preferably at least 80% of the overall protein weight, even more preferably at least 90% of the overall protein weight, yet more preferably at least 95% of the overall protein weight, and most preferably at least 99% of the overall protein weight of the preparation.

In a fifteenth aspect, the invention provides methods for identifying binding agents that are useful for regulating hyphal growth of fungi. The methods according to this aspect of the invention comprise treating a first wild-type fungus with a proposed binding agent to obtain a first result, treating a second mutant fungus with the same proposed binding agent to obtain a second result, and comparing the first and second results, wherein the mutant fungus is selected from the group consisting of a null mutant for CRV-1, a null mutant for CRV-2 and a null mutant for CRV-4. In certain preferred embodiments, the method is carried out in vitro. In certain other preferred embodiments, the method is carried out in vivo.

In a sixteenth aspect, the invention provides another method for identifying binding agents that are useful for regulating hyphal growth. In the method according to this aspect of the invention, a purified polypeptide according to the fourteenth aspect of the invention is contacted with a molecule that is a potential binding agent under condition under which such binding is detectable. Such binding assays are well known in the art and include enzyme-linked immunosorbant assays and radiolabel assays.

In a seventeenth aspect, the invention provides a binding agent specific for a protein selected from the group consisting of CRV-1, CRV-2 and CRV-4. As used herein, As used herein, a "binding agent" is a molecule or macromolecule which binds under physiological conditions to CRV-1, CRV-2, or CRV-4. "Binds under physiological conditions" means forming a covalent or non-covalent association with an affinity of at least $10^6 M^{-1}$, most preferably at least $10^9 M^{-1}$, either in the body, or under conditions which approximate physiological conditions with respect to ionic strength, e.g., 140 mM NaCl, 5 mM $MgCl_2$. A "population of molecules", as used herein, refers to a plurality of identical molecules. A "mixed population of molecules" refers to a plurality of molecules wherein more than one type of molecule is present.

In certain preferred embodiments, a binding agent according to the invention is a peptide or a peptidomimetic. For purposes of the invention, a "peptide" is as defined previously.

In certain preferred embodiments, such a binding agent comprises a complementarity determining region of an antibody which binds under physiological conditions to a peptide-containing epitope of CRV-1, CRV-2, or CRV 4, or a peptidomimetic of such a complementarity-determining region. For purposes of the invention, a "complementarity determining region of an antibody" is as defined previously.

Additional preferred binding agents according to the invention include small molecules, as that term has been defined previously.

The following examples are intended to further illustrate certain particularly preferred embodiments of the invention and are not intended to limit the scope of the invention.

EXAMPLE 1

Generation of Avirulent Mutant *Candida Albicans* Strains

To create homozygous knockouts of the genes crv-1, crv-2 and crv-4 (crv means *Candida* regulator of virulence), homologous recombination was used to replace the endogenous gene of interest with a selectable marker. The *Candida albicans* strain used as the parent cell line was BWP17 (ura3::imm434/ura3::imm434his1::hisG/his1::hisG arg4::hisG/arg4::hisG; Wilson, R B et al., J. Bacteriology 181: 1868-1874 (1999). This strain allows the use of ARG4, HIS1or URA3 as selectable markers.

PCR products were created to replace the endogenous gene in the *Candida albicans* genome. One set of primers contains a large stretch (60 base pairs) of homologous sequence to the gene of interest, which allows homologous recombination. These primers are listed as "GENE-5DR" or "GENE-3DR" for the 5' and 3' ends of the gene respectively (Table 1). A second set of primers flanking the region of integration was used as a diagnostic tool to determine the correct integration of the selectable marker (HIS1 or ARG4). These primers are listed as "GENE-diag" in (Table 1).

TABLE 1

PCR PRIMERS
Primer Sequences

| GENE | Microbia Primer Name | SEQUENCE |
|---|---|---|
| CRV1 | FLO8F-3DR | GAATTCGCCTTTTTACCCTTTTTACTATTGGATT CTTTCTTCGATTTCTTATTGCCCATTTGTGGAAT TGTGAGCGGATA (SEQ. ID. NO: 7) |
| CRV1 | FLO8F-5DR | GCTATATTTTGTTGCTTTTATTAATTTATTGGCT TTTTATTTTGTTTTGGTTTGTTTTGTGTTTTCCC AGTCACGACGTT (SEQ. ID. NO: 8) |
| CRV1 | FLO8F-diag | CGAACAGTATATCAAACTGCACTTT (SEQ. ID. NO: 9) |
| CRV1 | FLO8R-diag | ATGGCTGGAAATCCTTCTTT (SEQ. ID. NO: 10) |
| CRV2 | TEC1F-5DR | TAATTCACGTGTCCAAGACACTGACATCTGTCCA GATGATGATGAAGAAGCTTTTGAAGAAGTTTTCC CAGTCACGACGTT (SEQ. ID. NO: 11) |
| CRV2 | TEC1F-diag | CATCAACCTAATATGTATGAGAACG (SEQ. ID. NO: 12) |
| CRV2 | TEC1R-3DR | TCATTGATATCTGGCATTGATGCTGAATGAATGG TGTCTCGTATACCAGGAATTGAAGTTGTGTGGAA TTGTGAGCGGATA (SEQ. ID. NO: 13) |
| CRV2 | TEC1R-diag | TTTGGTGTGGTTGCAAGTGT (SEQ. ID. NO: 14) |

TABLE 1-continued

PCR PRIMERS
Primer Sequences

| GENE | Microbia Primer Name | SEQUENCE |
|---|---|---|
| CRV4 | 715F-5DR | ACATATAATTCTTTCATATTTTCATTTTATTTCA TACGTTAAGATCCATATCCAATAGTCATGGGTTT TCCCAGTCACGACGTT (SEQ. ID. NO: 15) |
| CRV4 | 715R-diag | GGTAAAAAACCTTCATTTAA (SEQ. ID. NO: 16) |
| CRV4 | 715R-3DR | CGGTAGTAAAAATATATCTATATCTCAAAGCGTG GAAATATATTCCCACTCGTCCAAAGTTGTGGAAT TGTGAGCGGATA (SEQ. ID. NO: 17) |
| CRV4 | 715R-diag | AGAAAAATACAAAGCCAATT (SEQ. ID. NO: 18) |

PCRs were carried out as follows. Plasmid DNA containing the selectable markers ARG4 or HIS1 was used for the template DNA. A 100 ul PCR reaction contained 1 ul plasmid DNA, 0.2 uM GENE-5DR and GENE-3 DR primers, 0.25 mM dNTP mixture, 2 mM $MgCl_2$, 1X ExTaq buffer (TaKara) and 0.5 ul ExTaq DNA Polymerase (TaKara). The thermocycler was programmed to heat the reaction at 94 C for 5 min; 30 cycles of 1 min at 94 C, 1 min at 55 C, 4 min at 72 C; and the last extension step at 72 C for 8 min. 5 ul of the PCR reaction was analyzed on agarose gels using ethidium bromide staining.

A saturated culture of BWP17 cells was diluted 1:100 in YPD+uridine and grown to log phase (OD600=0.8-1.0). These cells were washed, pelleted and resuspended in 1/50 volume of 1xLATE buffer (0.1 M lithium acetate, 10 mM Tris HCL (pH 7.5), 1 mM EDTA). Into a 2 ml 96 well plates (Beckman) was added 100 ul of the cell suspension (equivalent to about 20 ml of culture), 5 ul herring DNA, the PCR product described above and a PEG solution (40% polyethylene glycol 3350 in LATE buffer). This mixture was incubated overnight at 30 C. After heat shocking the cells for 1 hour at 42 C, the cells were washed, pelleted and plated onto selectable media. PCR was performed using the diagnostic primers described above and identified transformants containing the selectable marker inserted into our gene of interest.

Homozygous knockouts were created using the above transformation procedure but a heterozygous knockout was used in place of BWP17 as the parent cell line. In addition, a different selectable marker is used instead of what was used for creating the heterozygous mutant. When HIS1 was used to knock out the first copy of the gene, then ARG4 was used to knock out the second copy of the gene and visa versa. The double knockouts were confirmed using diagnostic primers as described above. For the homozygous knockouts, two PCR products at the molecular weights of the selectable markers, ARG4 and HIS1 were obtained.

EXAMPLE 2

Growth Characteristics of Mutant Strains

The mutant strains obtained according to Example 1 were tested under various growth conditions to assess the effect of the mutations on growth and invasion properties. crv1, crv2, and crv4 null mutant strains and a double mutant described in the prior art (efg1/cph1) were grown in liquid YPD+ uridine culture at 30 C. OD600 was measured over time.

Mid log OD measurements were used to calculate doubling times. The results are shown in FIG. 4. The growth rates of the mutant strains are comparable to that of a wild type control strain. These results demonstrate that crv-1, crv-2 and crv-4 are not required for growth.

The mutants were next grown under specific conditions that induce wild type *Candida albicans* to convert to growth in a filamentous invasive form (hyphae). First they were grown in "spider" medium (10 g nutrient broth, 10 g mannitol, 2 g K2 HP04 (dibasic), 13.5 g Bacto agar per liter) Ruffling indicates invasion. The results are shown in FIG. 5A. Crv1 and crv2 mutants showed no ruffling, in contrast to wild type *Candida*. Next, the strains were grown in agar with serum. 0.5 ml of serum was added to the surface of an agar plate (30 ml volume) and allowed to dry. *Candida* samples were then pipeted onto the surface of the plate and transferred to 37 C for three days. The results are shown in FIG. 5B. Crv1 and crv2 mutants did not form filaments and did not invade into the substrate. The strains were then grown on agar cornmeal plates (17 g cornmeal agar per liter) The results are shown in FIG. 5C. These results demonstrate that crv2 mutant will invade under certain nonphysiologic conditions, but crv1 does not. This indicates that crv2 is distinguishable from crv1 and could define nonoverlapping targets.

Figure 5D:
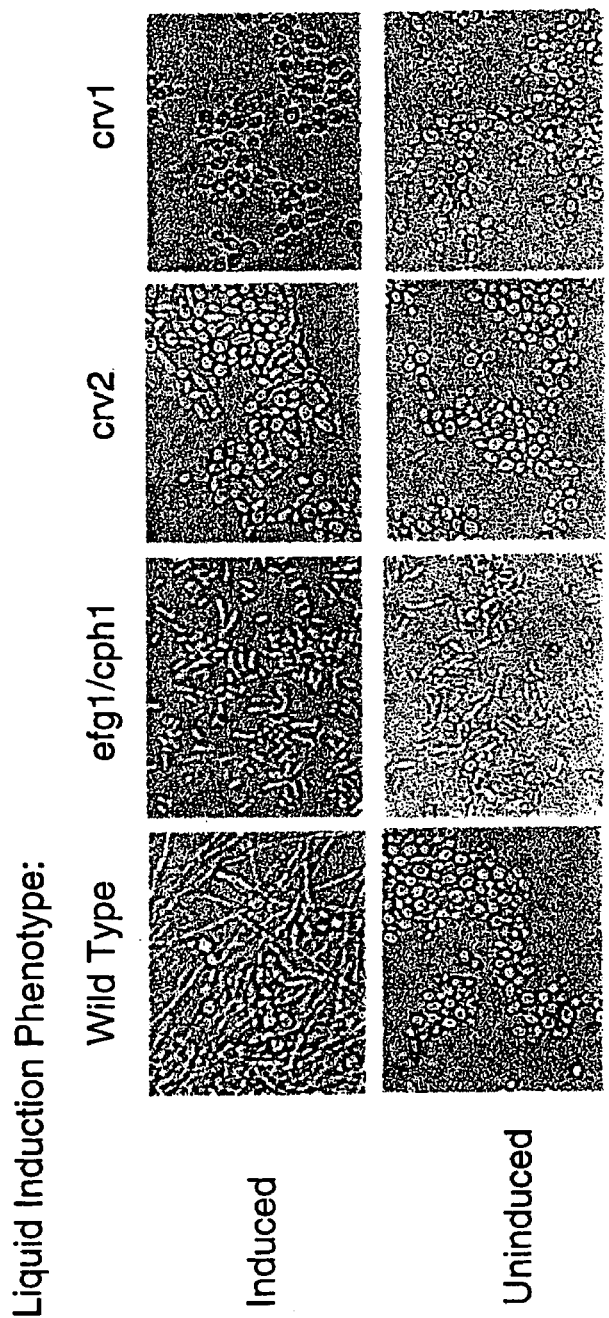

Finally, the strains were grown under physiologic filamentation-inducing conditions (neutral pH, serum, 37C) in liquid medium to demonstrate yeast and filament morphology. The results are shown in FIG. 5D. Crv1 and crv2 mutants were unable to form hyphae. Note the abnormal elongated morphology of efg1/cph1 cells.

Taken together, these results demonstrate that crv1 and crv2 are required for hyphal growth and invasion under physiological conditions, but do not otherwise produce an observable phenotype under the conditions tested. This is the first demonstration of an otherwise normal but non-invasive phenotype, strongly suggesting that invasion is essential to pathogenesis in view of Example 5, below.

EXAMPLE 3

Complementation Studies

Figure 6:
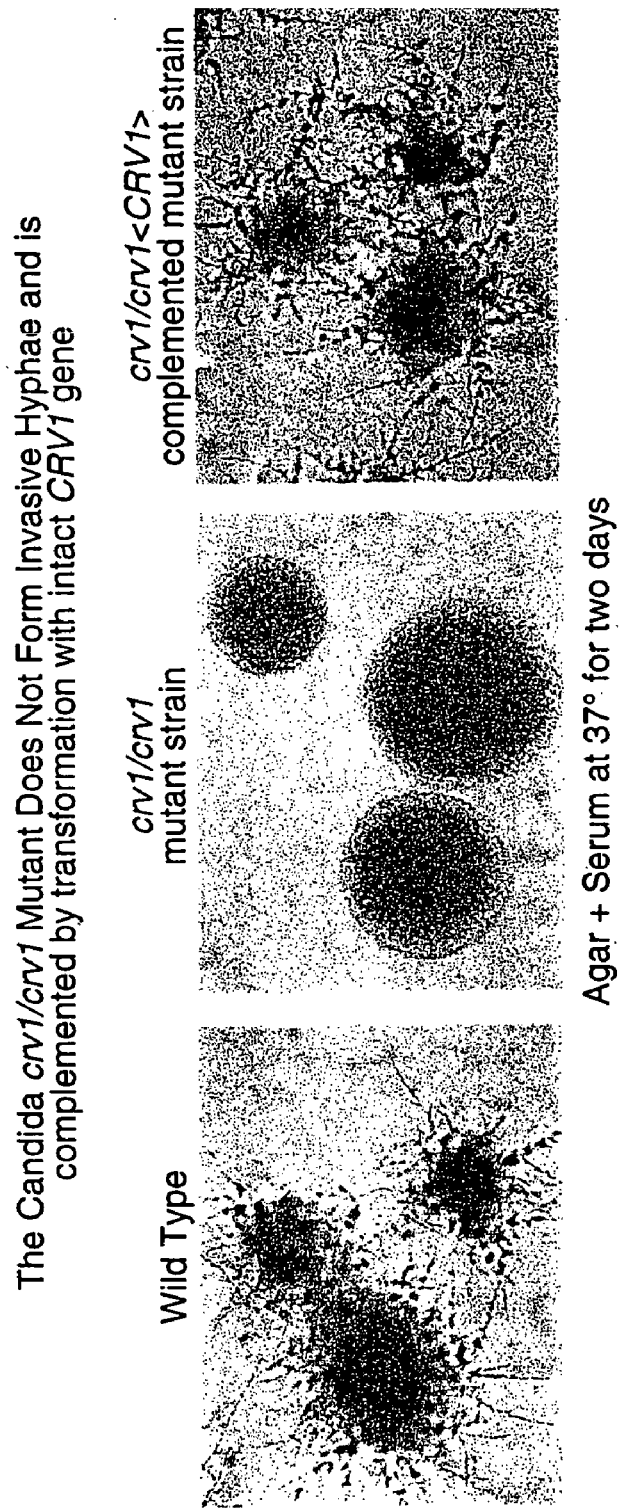
FIG. 6 shows phenotypes of three *C. albicans* strains (including crv1/crv1) on agar+serum.
Figure 7:
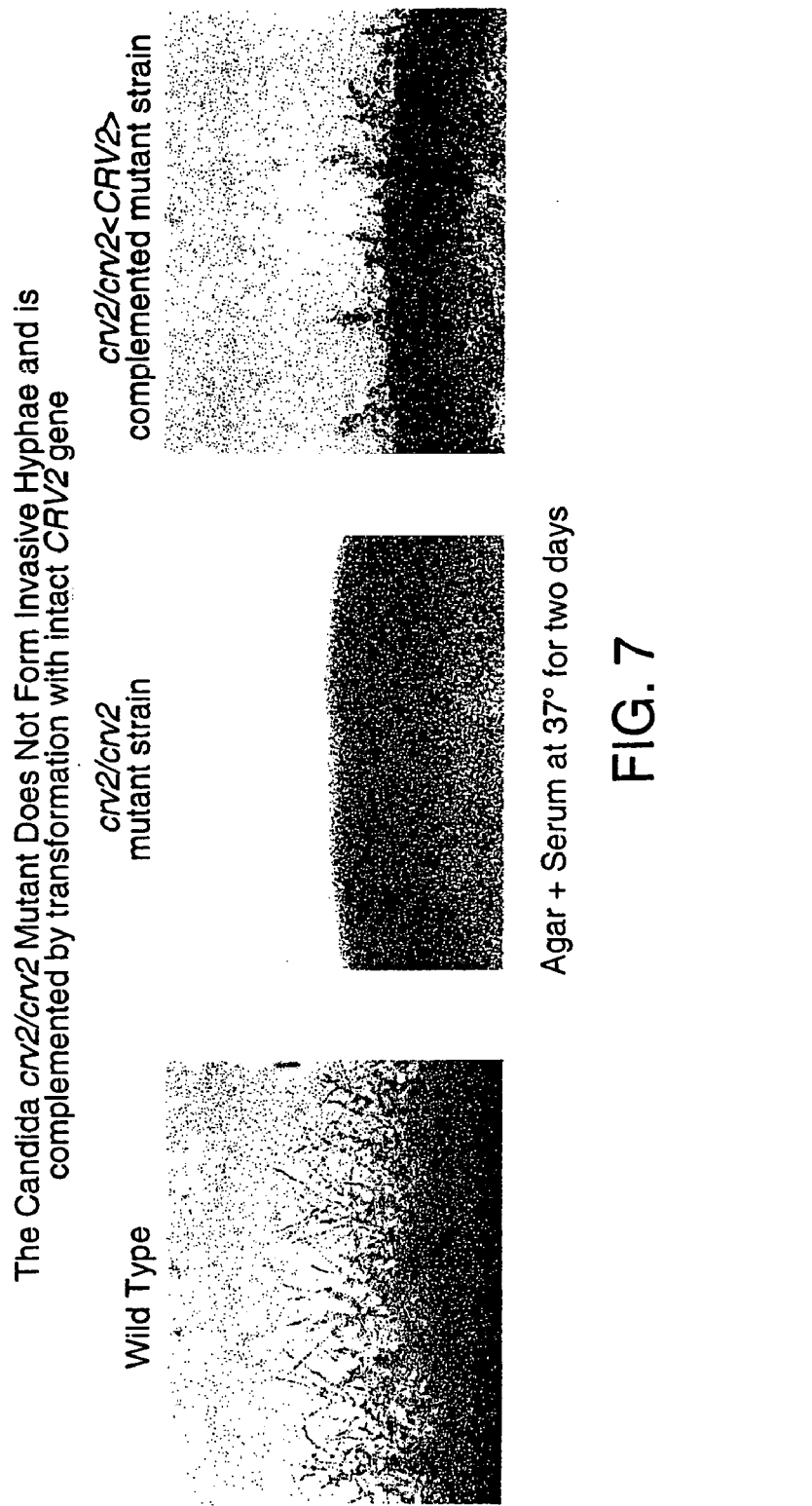
FIG. 7 shows phenotypes of three *C. albicans* strains (including crv2/crv2) on agar+serum.
Figure 8:
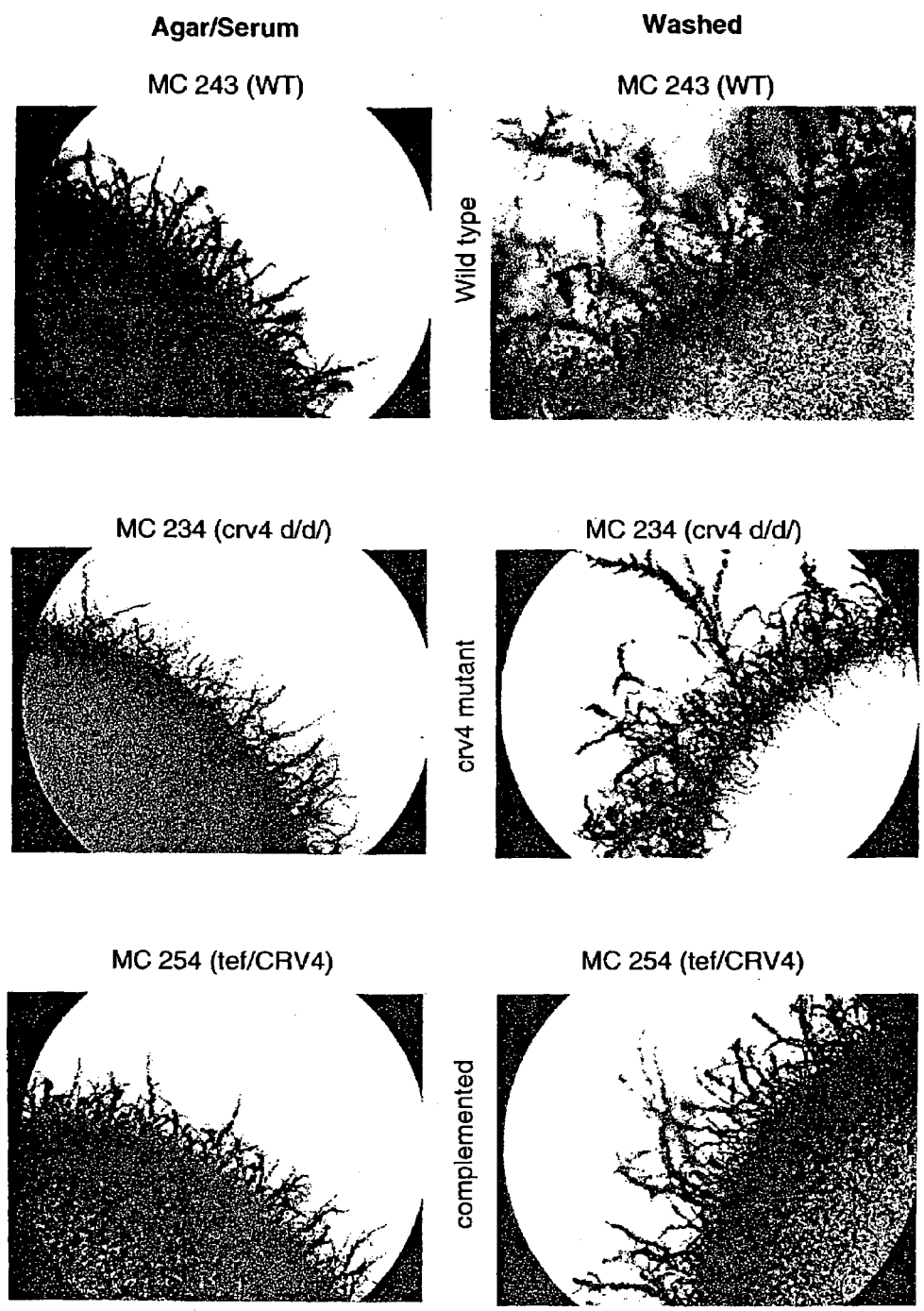
FIG. 8 shows phenotypes of three *C. albicans* strains (including crv4/crv4) on agar+serum.

To demonstrate that the modified behaviors of the mutant strains is due to the deletion of the genes of interest, each strain was complemented with the intact gene using standard transformation procedures. The results for crv1 are shown in FIG. 6. These results demonstrate that the crv2 gene is able to complement the null strain back to wild type phenotype. The results for crv2 are shown in FIG. 7. These results demonstrate that the crv2 gene is able to complement the null strain. The results for crv4 are shown in FIG. 8. On the left, wild type, the null strain and the complemented null strains are shown after 3 days at 37 degree on agar/serum plates. On the right, the same plate after 6 additional day incubation at room temperature was washed vigorously with tap water and rephotographed. Note the clearing zone inside the null strain that gives crv4 a visible phenotype.

EXAMPLE 4

Effect of crv 1 or crv2 Null Mutation on Adherence

Figure 9:
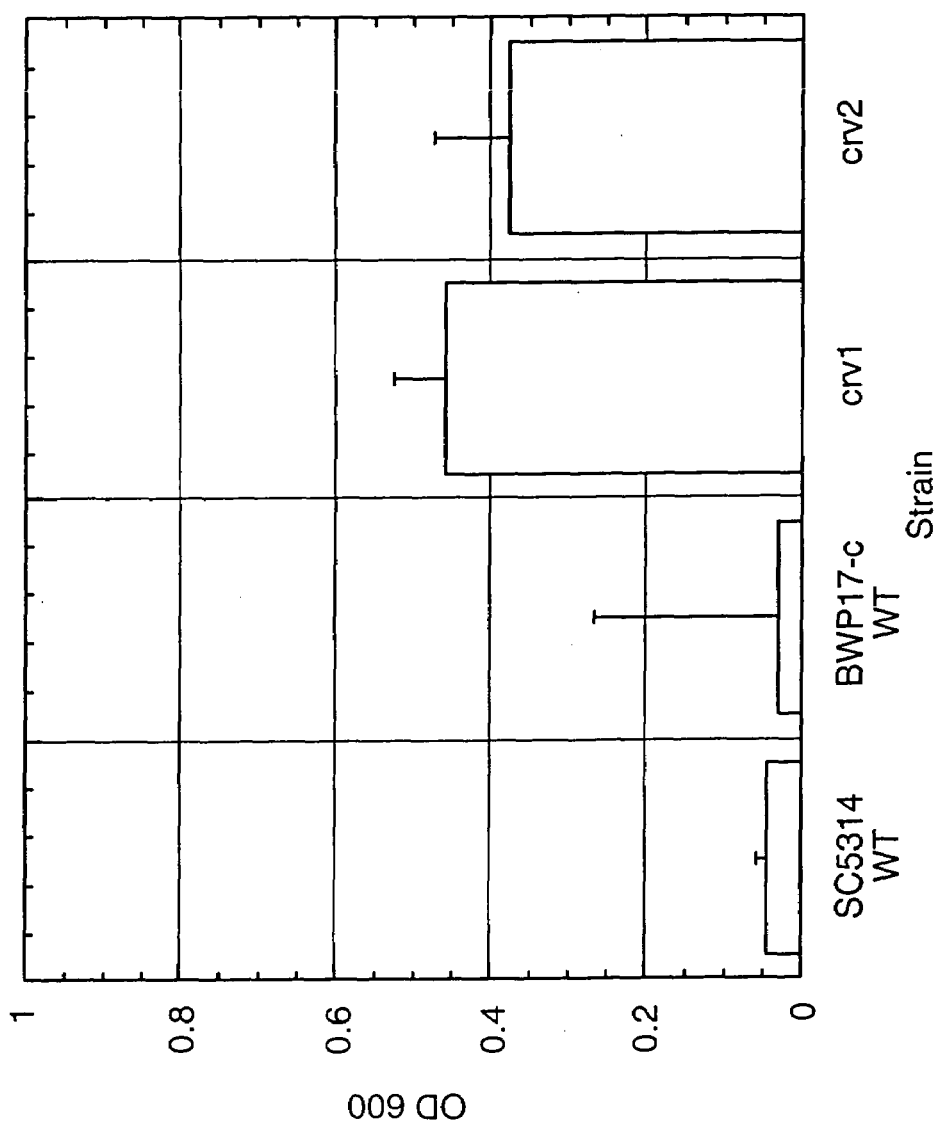
FIG. 9 shows relative turbidity of 4 strains of *C. albicans* growing in serum-containing broth.
Figure 10:
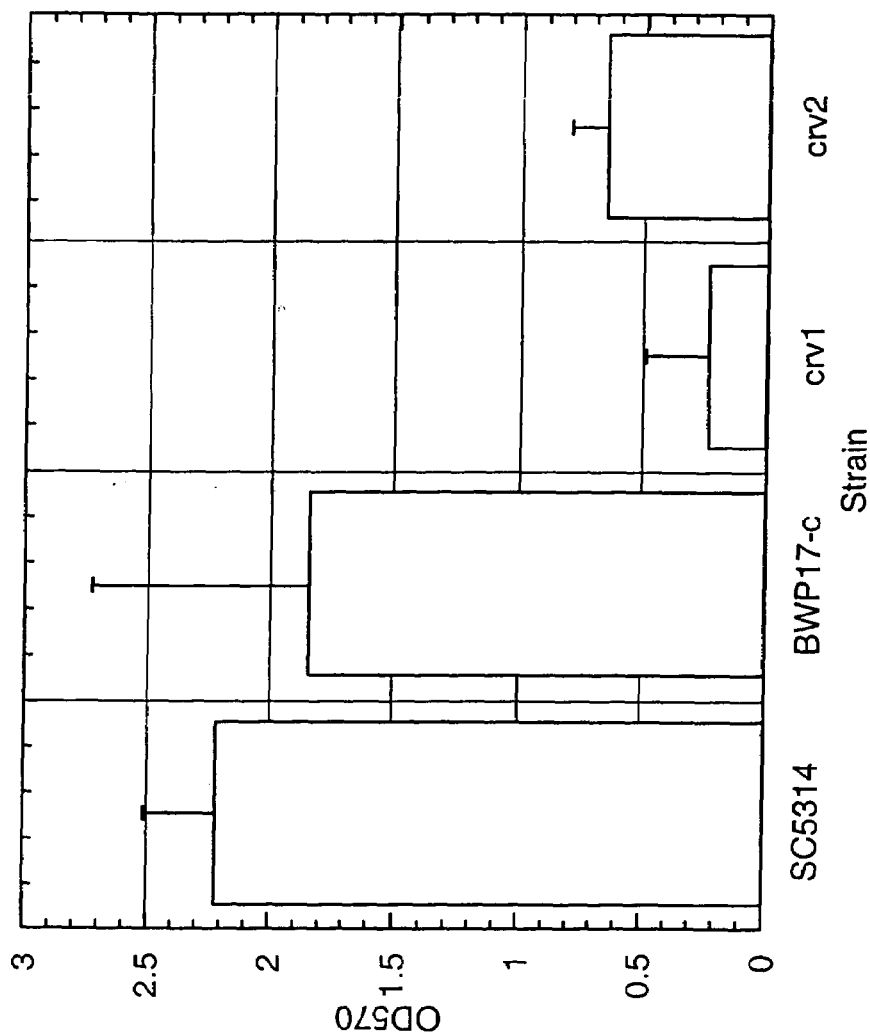
FIG. 10 shows relative adherence of 4 strains of *C. albicans*.

Mutant strains obtained according to Example 1 were tested for adherence as follows. 1:25 dilution of an YPD+Uri overnight culture of 2 wild type strains (Sc5314 and BWP17 complemented for auxotrophies and a crv1 and a crv2 strain grown in YNB pH 7.5/serum was grown in triplicate in PVC microtiter plates for 3 hr at 37 degree. Turdidity of the supernatant is an indication of the lack of adherence of the mutant strains, as shown in FIG. 9. The adherent pellet was rinsed and stained with 1% crystal violet. The OD 570 measures the relative adherence of wild type and mutant strains, as shown in FIG. 10. These results demonstrate that crv1 and crv2 are required for *Candida* adherence.

EXAMPLE 5

Effect of crv1, crv2 and crv4 Null Mutation on Hyphal-Specific Gene Expression

Figure 11:
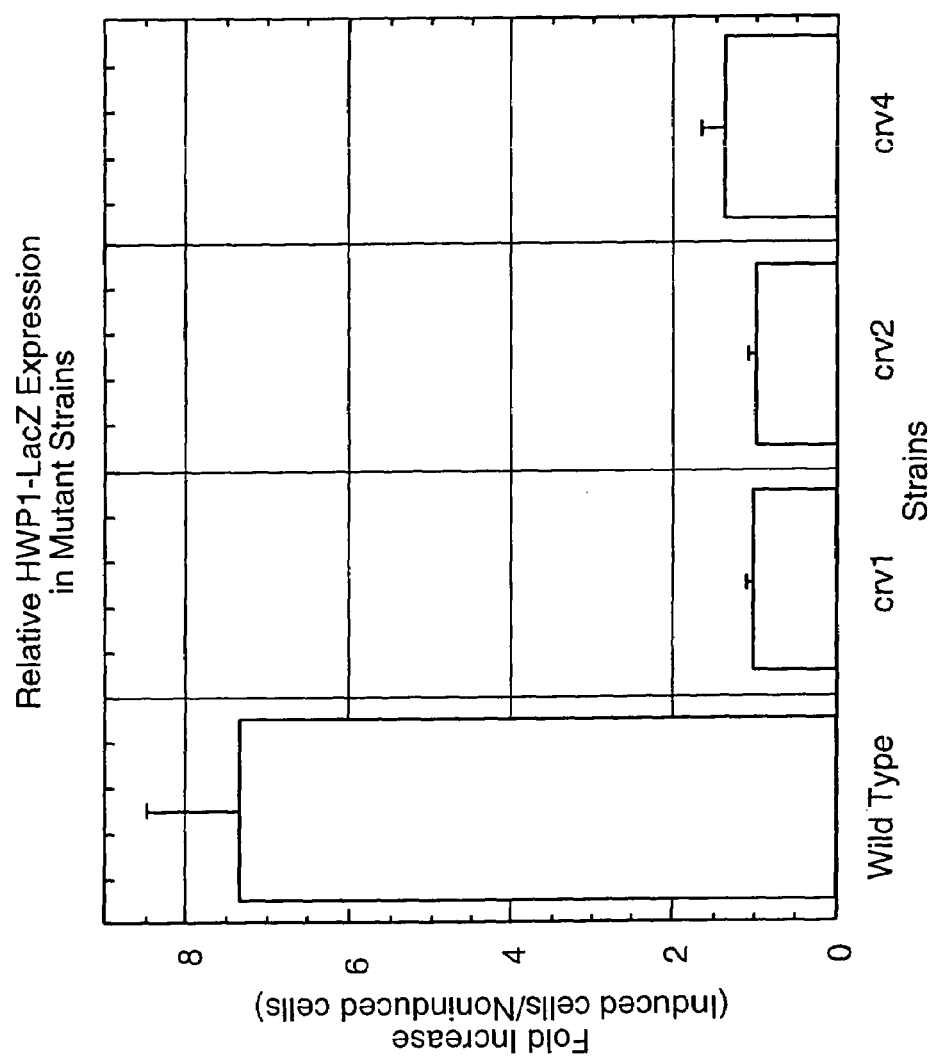
FIG. 11 shows the ratio of HWP1-LacZ expression of induced mutant and wild-type cells over non-induced cells.

The expression of the *Candida* HWP 1 gene is markedly induced when cells convert to filamentous growth (Staab et al., J Biol Chem 271: 6289-6305 (1996)). We used an HWP-LacZ reporter construct to measure the expression from the HWP1 promoter when wild type and mutant cells were exposed to filament inducing conditions for a defined period. The crv-1, crv-2 and crv-4 null mutants obtained according to example 1 and the parent strain were modified to contain the HWP1-LacZ reporter construct. The cells were grown in non-inducing conditions (YNB, pH 4.5, 30° C.) overnight and then grown in either inducing conditions (YNB, pH7.5, 37° C., 10% serum) or non-inducing conditions for three hours. LacZ expression was assayed after washing the cells with Z buffer (60 mM NA2 HPO4 (anhydrous), 40 mM NA2 HPO4-H2O, 10 mM KCl, 1 mM MgSO4-7H2O) and lysing the cells with detergents in Z buffer (2 mg/ml CTAB, 0.1 mg/ml deoxycholate, 7.7 mg/ml 2-ME). The reaction was run at 37° C. with 4 mg/ml ONPG as the substrate and stopped with 1M Na2CO3. OD420 was measured to assay the extent of LacZ expression in the cell and this value was normalized to the number of cells as measured by OD600. The results are shown in FIG. 11. In wild-type cells there was a 4.5-fold increase in HWP1-LacZ expression upon induction. In the crv1 mutant, HWP1-LacZ expression is the same in the induced cells and the non-induced cells. These results demonstrate that that crv1 and crv2 are required for the expression of the HWP1 promoter, a hyphal specific protein promoter.

EXAMPLE 6

Effect of crv1 or crv2 Null Mutation on Pathogenicity

Figure 12A:
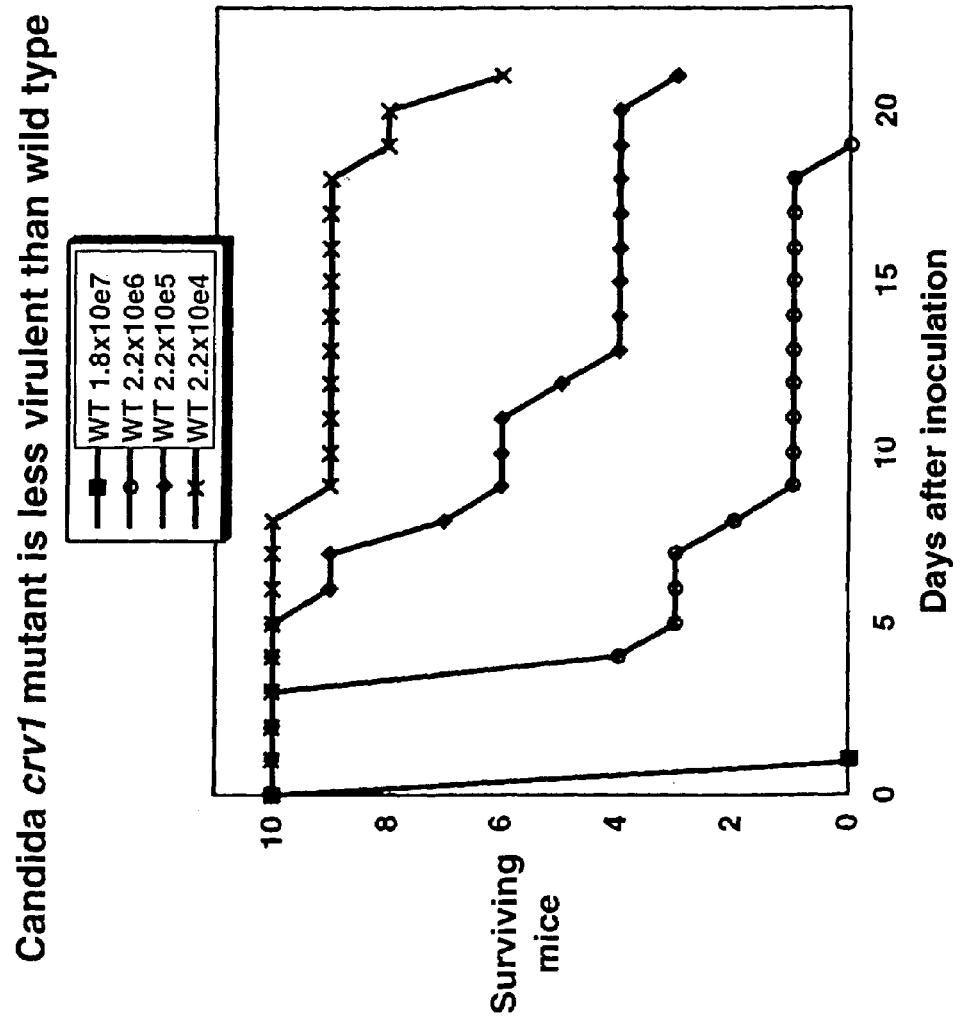
FIGS. 12A-12C shows survival curves for mice injected *C. albicans*. strains, including wild-type, crv1 mutant, and crv1 mutant complemented with the CRV1 gene.
Figure 12B:
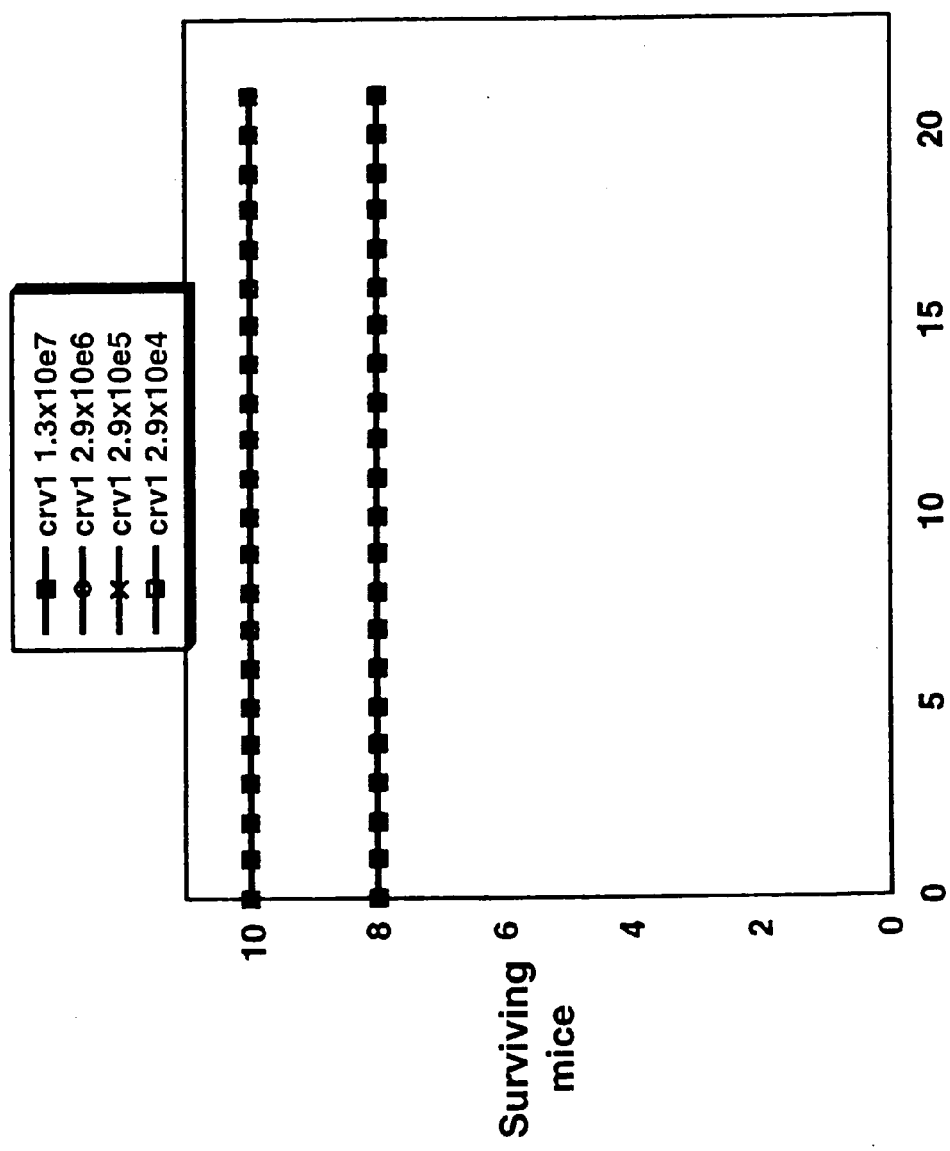
Figure 12C:
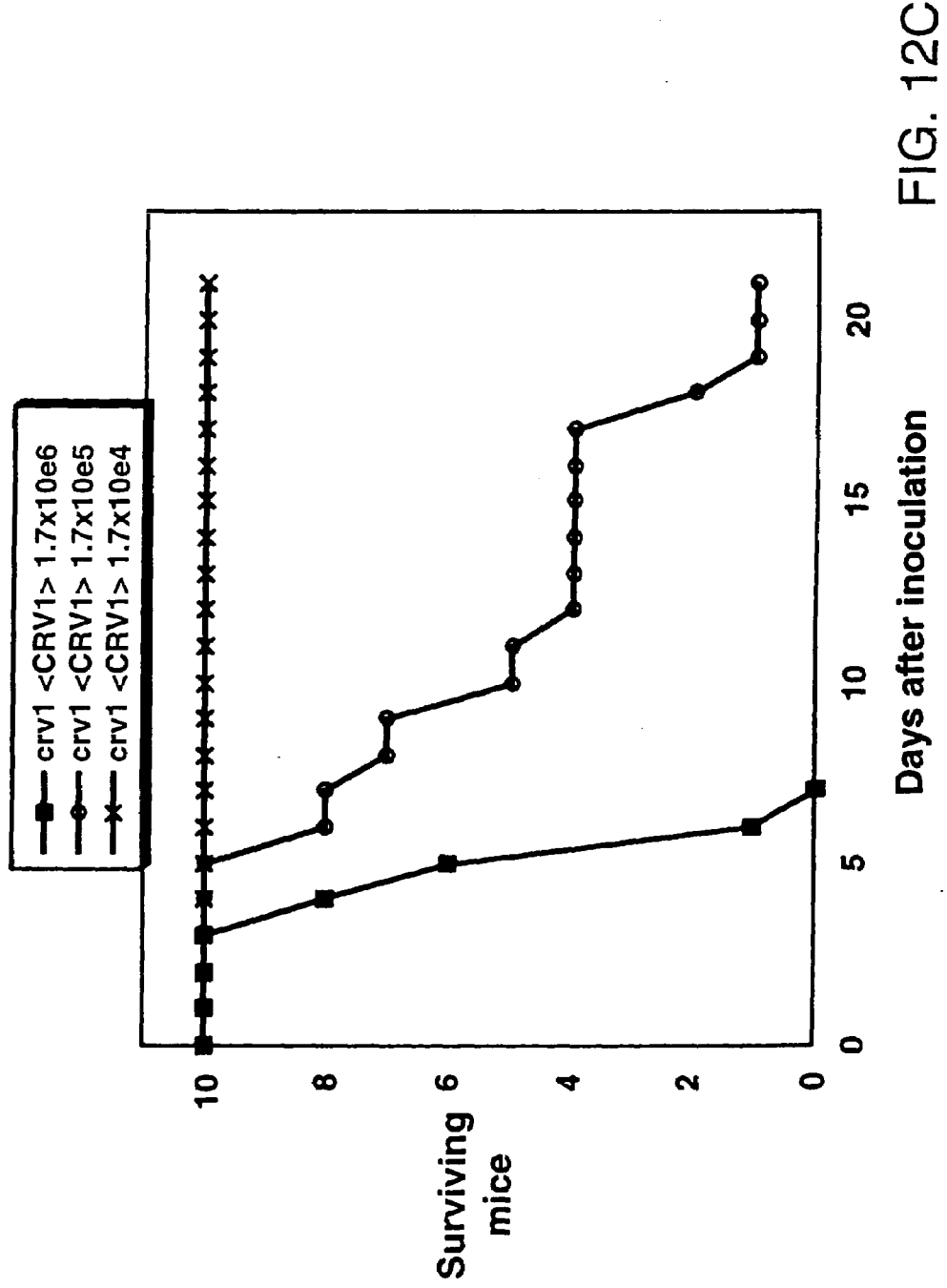
Figure 13A:
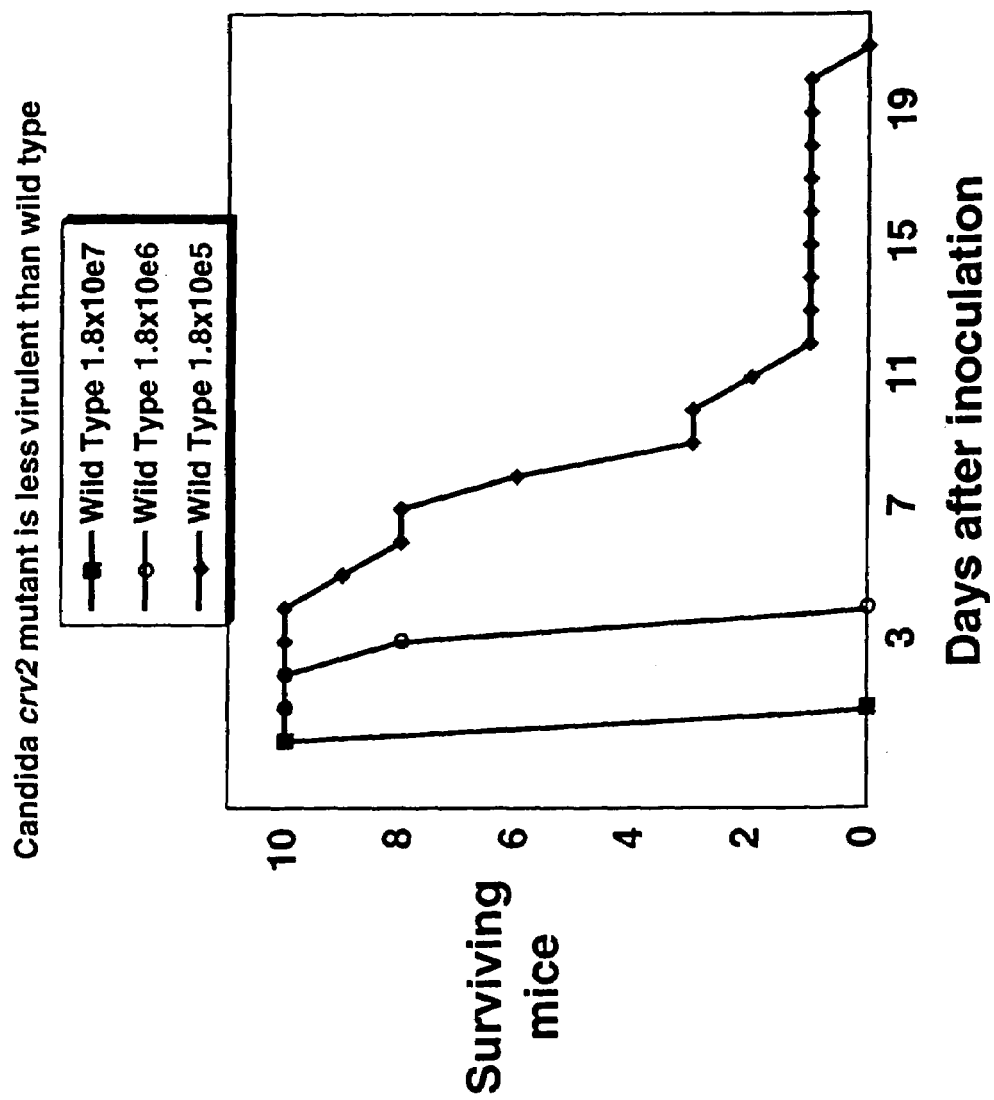
FIGS. 13A-13B shows survival curves for mice injected with wild-type *C. albicans*, or with the crv2 mutant.
Figure 13B:
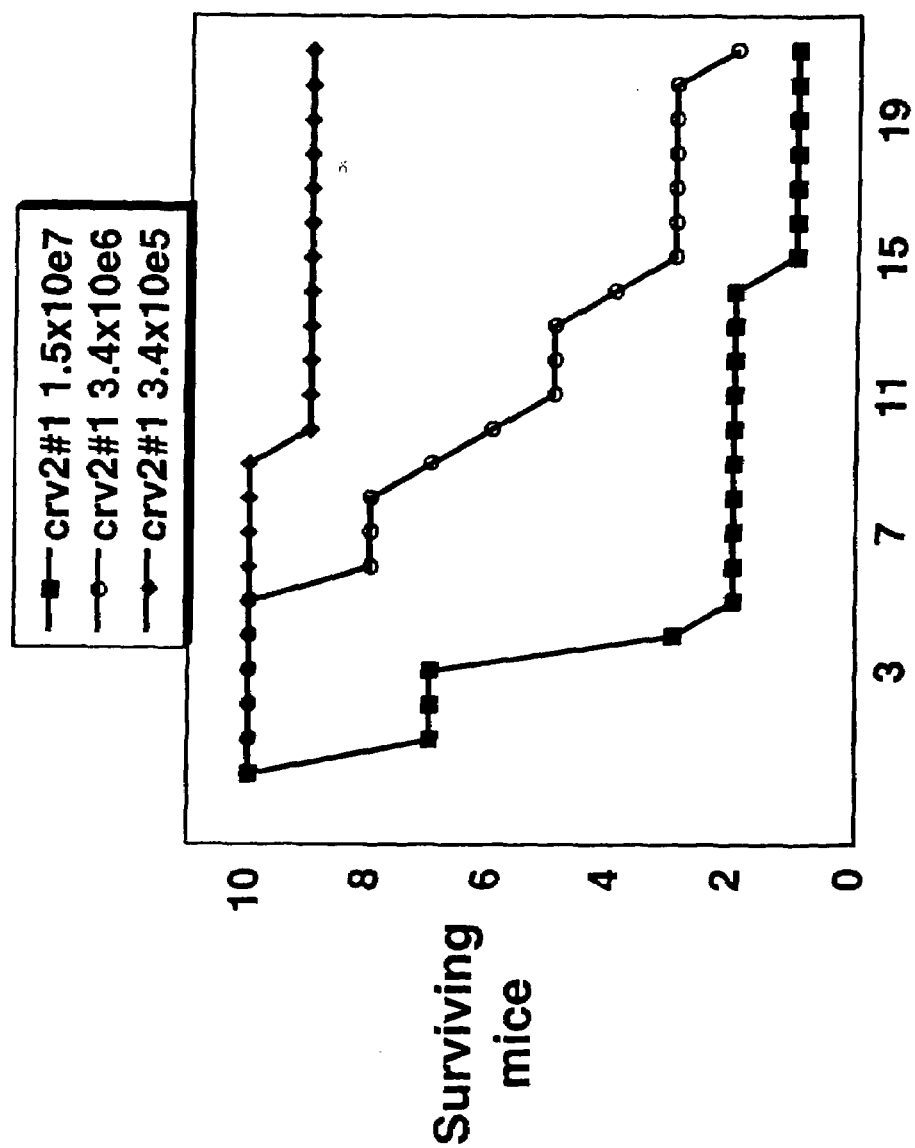

Genetically defined strains of *Candida albicans* were injected intravenously into juvenile, C57B mice (Charles River Labs) at defined inocula via the tail vein and the survival of the mice over a three week period were measured. The strains used were the crv1 and crv2 null mutants obtained according to Example 1 and the parent strain. The results are shown for wild-type, crv1 null mutant and crv1 null mutant complemented with the CRV1 gene in FIGS. 12A-12C. Fifty percent lethality was obtained with an inoculum as low as 220,000 cells/mouse with the parent strain. In contrast, as shown in FIGS. 12A-12C, even 10 times that inoculum of the crv1 null mutant did not produce lethality. Similarly, the results for the crv2 mutant are shown in FIGS. 13A-13B. Histology of the crv1 mutant infected mice demonstrated that the mice had cleared the *Candida* from their systems. These results demonstrate that crv1 and crv2 are required for virulence. Thus, these results demonstrate that compounds that block the behavior that is regulated by crv1 or crv2 are candidates for antifungal drugs.

EXAMPLE 7

Effect of Inhibitors of Hyphal Growth on Invasion

Figure 14:
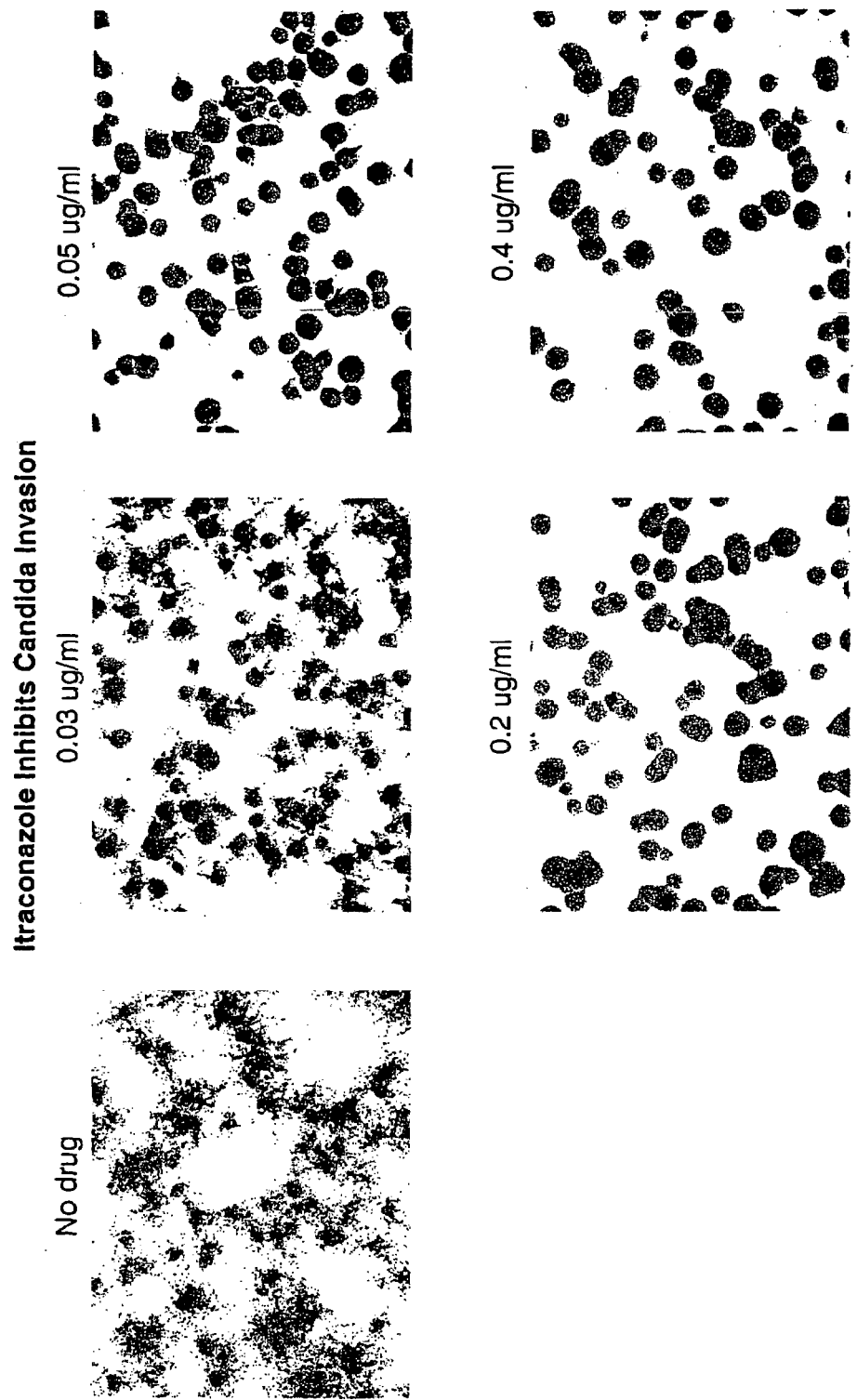
FIG. 14 shows a *Candida* agar invasion assay in the absence and presence of different concentrations of Itraconazole.

Cells were pre-grown overnight in YPD at 28 C, then diluted serially with 5× dilutions to give samples containing approx 10,000 CFU per ml. Plates were prepared with agar+drug, dried, supplied with 0.5 ml serum and dried again. 3 ul spots of cells were spaced >1 cm apart to yield approx 100 colonies per spot. Plates were incubated 2 days at 37 C. Photo micrographs were evaluated for colony growth and invasion. Photos were taken of colonies at 40× magnification. The results are shown in FIG. 14. Drug concentrations are indicated on the figure. In the absence of drug, *Candida* invades extensively. In the presence of drug, invasion is inhibited but the cells continue to grow. As little as 1/8-1/16 MIC itraconazole was able to inhibit invasion.

EXAMPLE 8

Treatment of Active *C. albicans* Infection with Sub-Inhibitory Doses of Itraconazole Initially, an optimal inoculum is established, i.e. the inoculum that results in 50-100% mortality over two weeks, but with a window of time (>2 days) where there is little or no mortality. Mice are then inoculated at the optimal inoculum and colony forming units per weight tissue are measured over time and tissue histology is also followed over time. For example, 30 mice are inoculated with ~$3 \times 10^5$, (and 10 mice at $1 \times 10^6$ for 2-3 hr, 1d, 2d times only). Three mice are sacrificed at each interval: 2-3 hr, 1d, 2d, 4d, 7d, 10d, 14d. For each mouse colony forming units in kidney, liver, spleen are measured; and selected histologic analyses are performed.

Prophylaxis—This experiment will measure the capacity of azole drugs to prevent the lethal consequences of systemic *Candida* infection at doses below the dose required to kill *Candida* in vivo. Treatment of experimental mice is initiated in groups defined by specific doses of azole (e.g. fluconazole). All mice are inoculated with the optimal inoculum and then, at a given time based on the preparatory experiment, half of the mice in each group are sacrificed and checked for tissue infection by measuring the colony forming units per gram of tissue. In addition, histology is performed on tissue samples to determine the morphology of remaining *Candida* cells. The remaining mice in each group are monitored for mortality and colony forming units per gram in the tissues of mice surviving to the experimental endpoint (at 2-3 weeks) are measured.

Treatment—This experiment will test the ability of azoles to cure established systemic *Candida* infection at doses below the dose required to kill *Candida*. Mice are inoculated with the optimal inoculum determined in the preparatory experiment. Treatment is initiated with various doses of fluconazole at a time indicated by the preparatory experiment. At a predetermined time(s) one half of the mice in each group are sacrificed to evaluate levels of tissue infection and for histological analysis (at approximately 2, 4, 7, and/or 10 days). The remaining mice in each group are monitored for mortality and colony forming units per gram in the tissues of mice surviving to the experimental endpoint (at 2-3 weeks) are measured.

---

What is claimed is:

1. An isolated nucleic acid molecule comprising the nucleotide sequence of SEQ ID NO:1.

2. The isolated nucleic acid molecule of claim 1 consisting essentially of the nucleotide sequence of SEQ ID NO:1.

3. An isolated nucleic acid molecule comprising a nucleotide sequence encoding a polypeptide comprising the amino acid sequence of SEQ ID NO:2.

4. The isolated nucleic acid molecule of claim 3 comprising a nucleotide sequence encoding a polypeptide consisting essentially of the amino acid sequence of SEQ ID NO:2.

5. The isolated nucleic acid molecule of claim 3 comprising a nucleotide sequence encoding a polypeptide consisting of the amino acid sequence of SEQ ID NO:2.

6. A vector comprising the isolated nucleic acid molecule of any of claims 1, 2 and 3-5.

7. A host cell containing the isolated nucleic acid molecule of any of claims 1,2 and 3-5.

8. A host cell containing the vector of claim 6.

* * * * *

UNITED STATES PATENT AND TRADEMARK OFFICE
CERTIFICATE OF CORRECTION

PATENT NO. : 7,291,720 B2  Page 1 of 1
APPLICATION NO. : 10/278703
DATED : November 6, 2007
INVENTOR(S) : Brian M. Cali It is certified that error appears in the above-identified patent and that said Letters Patent is hereby corrected as shown below:

Title page, column 1, item (75); under Inventors: replace inventor "Todd Milne" with --G. Todd Milne--

Signed and Sealed this

Thirteenth Day of January, 2009

JON W. DUDAS
*Director of the United States Patent and Trademark Office*

SEQUENCE LISTING

<160> NUMBER OF SEQ ID NOS: 21

<210> SEQ ID NO 1
<211> LENGTH: 2448
<212> TYPE: DNA
<213> ORGANISM: Candida albicans

<400> SEQUENCE: 1

```
atgaatcata aacaagtact accagaaaat gaaccgatat caacaacaac agcaactcca      60
tcatcatcca atactatggt tcccaacaca actaaacagg ttttaaactc gttgattttg     120
gattttttgg tcaaacatca atttcaagat acagcaaaag cattttctaa agaaagtccc     180
aatttgcctt ctattcctcc tttgatggat tgttctcaag gattttttatt ggaatggtgg     240 caagttttct ttgatttatt tcaagtcaga tatggagacg gtaacagtaa taataaccct     300
aacaacaagc tttatcatga ttatctcaga gtccaagaaa ctcaaaaaca tcttttcagt     360
caacttcctc ttatacagca gcagcaacaa caacaacatc actttcaaca acaacagcaa     420
caacaagggc aacagggaca gcctttcctg cagcaacagc aaagaggaat cggtgttgct     480
agtggtatgc aaaatcaaca acatcaattt gccccacagc atcaaggcca acctcaagga     540
ccaggtcaaa cacctcaacc gccaggttct gcaactaacg ctaatttccc tatcaatatg     600
ccaccaaatc tgaatcctca acaacaaatg ttccccatta atcaacaatt tgctcagatg     660
ccaaatggtc aaaatcagcc ttcaatggaa caacaacaaa gaatggcaat gatgatgaaa     720
caacaagcaa tggctgcaca aagacaacaa atcccaatga atggtttaga tccacaacaa     780
```

```
caacagcaaa tgatgaatgc tgtaggtggt ggacctggta atttgaattt gcaacaacaa    840 ctattttttac aacaacaaca gcagcagcag caacccaaaa ctactttcca gcaacaagca    900
caaaatcaaa tgaacaattt gcgtcaacaa gctgcaatgg ttgctcagca gcagcaacag    960
caacagcaac agcaacaaca acagggtcag ttgcaaggca atttgacatc agcaatgggt   1020
gattcatctc tgaagaataa ctctcctgtt ggtgcaagat caaatcaaca gctgactcca   1080
caacaaaatg ctgcaccagc ttcactgcca catccttctc aacaaggtca agcacaagct   1140
caacataact tccagagcca tcaacaacaa caacagcaaa tgactaagat ggctgggtct   1200
caaggaatga aaaagaatgg tcagatgtca acggcacta gtaataacag tagtggcaga   1260
aacaataatg ctctacgaga ttatcaaaat caattaatgt tattagaaag acagaataaa   1320
gagagattag aatttgctag aaacactggt aattccgact ccaacccatt gagtaatgga   1380
atgatgtttg ccggtcaaaa tcaatattca aattcaaatc aaaatcaaaa tcaacttcct   1440
cctaatcaac aacaaccaac tccagcaact ttccacccac cacctccgcc aacaactgca   1500
aatggtcctc agggacaatt taatcaaaaa ccatcacctg caacgtcaaa caattcacct   1560
gcattaggca ataaatcatc accagcaatg ggcaataaga atcgaagaa agaatccaat   1620 agtaaaaagg gtaaaaaggc gaattcaaat gcttctacaa cagcaaacaa caaaacatct   1680
ggacaaacaa caccaaacat gtcacaacct cctagtgctg gcacggagca aaagcagcct   1740
caaccaacag agcaaatgcg tcaattacaa gacaagcaac agcgtccagg ttcaaatact   1800
ccaagtatgg gaaagaagga tttccagcca ttgacacctc gctctgaacc aattagcggt   1860
gaaactacga aaagaagcg taaatcaggt aaattgaatg acaataatga aaatagtaat   1920
ggcaattctc caagaagca agccaaaacc aatgcaaact ccaaaaactt agatcctata   1980
ataaaagaag aagagaatgg agtattatct ttgaagaaag aatcttcaac ttcgttacaa   2040
gatcaagatc tagattaaaa ccccccattg gcaccaactc aagccactgc tatgtccaat   2100
acatttaacg acgatccatt tgatgttcat ttattagata cacaacatca tcaccaacaa   2160
aatagcaaca cagcaatca taatcgtggg caaaatcttt caaatggaag taataatctc   2220
agtgtaagtg gcccaggaat gggaatgaat aatctggtat ttggtgattc gactcatgca   2280
tttgacatta atttcaacat tgatagtctt gatgatatat ggacaactac tggaccagga   2340
ggtgatatta ctggcactgg ttcgggttca ggaggtgctg gcggtaccga tgatgataac   2400
ttcatgggaa tgaattgggc tgcagatcca attgaaaatg gagattag                2448
```

<210> SEQ ID NO 2
<211> LENGTH: 815
<212> TYPE: PRT
<213> ORGANISM: Candida albicans

<400> SEQUENCE: 2

```
Met Asn His Lys Gln Val Leu Pro Glu Asn Glu Pro Ile Ser Thr Thr
 1               5                  10                  15

Thr Ala Thr Pro Ser Ser Ser Asn Thr Met Val Pro Asn Thr Thr Lys
            20                  25                  30

Gln Val Leu Asn Ser Leu Ile Leu Asp Phe Leu Val Lys His Gln Phe
        35                  40                  45

Gln Asp Thr Ala Lys Ala Phe Ser Lys Glu Ser Pro Asn Leu Pro Ser
    50                  55                  60

Ile Pro Pro Leu Met Asp Cys Ser Gln Gly Phe Leu Leu Glu Trp Trp
65                  70                  75                  80
```

```
Gln Val Phe Phe Asp Leu Phe Gln Val Arg Tyr Gly Asp Gly Asn Ser
                 85                  90                  95

Asn Asn Asn Pro Asn Asn Lys Leu Tyr His Asp Tyr Leu Arg Val Gln
            100                 105                 110

Glu Thr Gln Lys His Leu Phe Ser Gln Leu Pro Leu Ile Gln Gln Gln
            115                 120                 125

Gln Gln Gln Gln His His Phe Gln Gln Gln Gln Gln Gln Gly Gln
130                 135                 140

Gln Gly Gln Pro Phe Leu Gln Gln Gln Arg Gly Ile Gly Val Ala
145             150                 155                 160

Ser Gly Met Gln Asn Gln His Gln Phe Ala Pro Gln His Gln Gly
                165                 170                 175

Gln Pro Gln Gly Pro Gly Gln Thr Pro Gln Pro Pro Gly Ser Ala Thr
            180                 185                 190

Asn Ala Asn Phe Pro Ile Asn Met Pro Pro Asn Leu Asn Pro Gln Gln
            195                 200                 205

Gln Met Phe Pro Ile Asn Gln Gln Phe Ala Gln Met Pro Asn Gly Gln
    210                 215                 220

Asn Gln Pro Ser Met Glu Gln Gln Gln Arg Met Ala Met Met Met Lys
225                 230                 235                 240

Gln Gln Ala Met Ala Ala Gln Arg Gln Gln Ile Pro Met Asn Gly Leu
                245                 250                 255

Asp Pro Gln Gln Gln Gln Met Met Asn Ala Val Gly Gly Gly Pro
            260                 265                 270

Gly Asn Leu Asn Leu Gln Gln Leu Phe Leu Gln Gln Gln Gln Gln
    275                 280                 285

Gln Gln Gln Pro Lys Thr Thr Phe Gln Gln Ala Gln Asn Gln Met
290                 295                 300

Asn Asn Leu Arg Gln Gln Ala Ala Met Val Ala Gln Gln Gln Gln Gln
305                 310                 315                 320

Gln Gln Gln Gln Gln Gln Gln Gly Gln Leu Gln Gly Asn Leu Thr
                325                 330                 335

Ser Ala Met Gly Asp Ser Ser Leu Lys Asn Asn Ser Pro Val Gly Ala
            340                 345                 350

Arg Ser Asn Gln Gln Leu Thr Pro Gln Gln Asn Ala Ala Pro Ala Ser
    355                 360                 365

Leu Pro His Pro Ser Gln Gln Gly Ala Gln Ala Gln His Asn Phe
    370                 375                 380

Gln Ser His Gln Gln Gln Gln Gln Met Thr Lys Met Ala Gly Ser
385                 390                 395                 400

Gln Gly Met Lys Lys Asn Gly Gln Met Ser Asn Gly Thr Ser Asn Asn
                405                 410                 415

Ser Ser Gly Arg Asn Asn Asn Ala Leu Arg Asp Tyr Gln Asn Gln Leu
            420                 425                 430

Met Leu Leu Glu Arg Gln Asn Lys Glu Arg Leu Glu Phe Ala Arg Asn
            435                 440                 445

Thr Gly Asn Ser Asp Ser Asn Pro Leu Ser Asn Gly Met Met Phe Ala
    450                 455                 460

Gly Gln Asn Gln Tyr Ser Asn Ser Asn Gln Asn Gln Asn Gln Leu Pro
465                 470                 475                 480

Pro Asn Gln Gln Gln Pro Thr Pro Ala Thr Phe His Pro Pro Pro
            485                 490                 495

Pro Thr Thr Ala Asn Gly Pro Gln Gly Gln Phe Asn Gln Lys Pro Ser
```

```
                500              505              510
Pro Ala Thr Ser Asn Ser Pro Ala Leu Gly Asn Lys Ser Ser Pro
        515                  520              525
Ala Met Gly Asn Lys Lys Ser Lys Lys Glu Ser Asn Ser Lys Lys Gly
    530                  535              540
Lys Lys Ala Asn Ser Asn Ala Ser Thr Thr Ala Asn Asn Lys Thr Ser
545                  550              555                  560
Gly Gln Thr Thr Pro Asn Met Ser Gln Pro Ser Ala Gly Thr Glu
                565              570              575
Gln Lys Gln Pro Gln Pro Thr Glu Gln Met Arg Gln Leu Gln Asp Lys
            580              585              590
Gln Gln Arg Pro Gly Ser Asn Thr Pro Ser Met Gly Lys Lys Asp Phe
        595              600              605
Gln Pro Leu Thr Pro Arg Ser Glu Pro Ile Ser Gly Glu Thr Thr Lys
        610              615              620
Lys Lys Arg Lys Ser Gly Lys Leu Asn Asp Asn Asn Glu Asn Ser Asn
625              630              635                  640
Gly Asn Ser Pro Lys Lys Gln Ala Lys Thr Asn Ala Asn Ser Lys Asn
            645              650              655
Leu Asp Pro Ile Ile Lys Glu Glu Asn Gly Val Leu Ser Leu Lys
            660              665              670
Lys Glu Ser Ser Thr Ser Leu Gln Asp Gln Asp Leu Asp Leu Asn Pro
        675              680              685
Pro Leu Ala Pro Thr Gln Ala Thr Ala Met Ser Asn Thr Phe Asn Asp
        690              695              700
Asp Pro Phe Asp Val His Leu Leu Asp Thr Gln His His Gln Gln
705              710              715                  720
Asn Ser Asn Asn Ser Asn His Asn Arg Gly Gln Asn Leu Ser Asn Gly
                725              730              735
Ser Asn Asn Leu Ser Val Ser Gly Pro Gly Met Gly Met Asn Asn Leu
            740              745              750
Val Phe Gly Asp Ser Thr His Ala Phe Asp Ile Asn Phe Asn Ile Asp
        755              760              765
Ser Leu Asp Asp Ile Trp Thr Thr Thr Gly Pro Gly Gly Asp Ile Thr
770              775              780
Gly Thr Gly Ser Gly Ser Gly Gly Ala Gly Gly Thr Asp Asp Asp Asn
785                  790              795                  800
Phe Met Gly Met Asn Trp Ala Ala Asp Pro Ile Glu Asn Gly Asp
                805              810              815

<210> SEQ ID NO 3
<211> LENGTH: 2232
<212> TYPE: DNA
<213> ORGANISM: Candida albicans

<400> SEQUENCE: 3
atgatgtcgc aagctactcc tagtgctact cccgtgagaa atgccgatgg acaaaagaaa     60
ggcaagaagc ttccattaat tgttgatgtt gcaattggta ataatggtaa gcaactttac    120
caggtacacg aatcttccaa gatggtaaga aaggaaatgc caagatctac caattttgct    180
ttgaatgatg acatttctga tgaagggttt tttataagcc aaataaatga acaaagaact    240
cccattagaa agactttggg tactttgtct ccatctagtc tcaaccaaaa gagaatccgc    300
catgatgtgt acgaccaagg agatgacaat agcaatgacg ataattgcca aaatgatgtt    360
```

```
tatgagcaac aacaacaaca accacagcaa caacaacaac aacaacaaca acttcatcaa      420
cctaatatgt atgagaacgg caacgttggg gttatttcca atgatccagt gtcttctgtt      480
ggccactatg acaacaaccc agtttcacat gtacctactg gtgcttattc acgtgtccaa      540
gacactgaca tctggtcaga tgatgttgaa gaagcttttg aagaagtgtt gagacttatt      600
ccaaagagtg gtttgaacaa aataaagatt gccggtagat cttgtggtag aaatgaatta      660
atatcagatt acattttgc caaaccggg aaattcagaa caagaaagca agtgtcctct        720
cacattcaag tgattaagaa tttaggacaa aaactcgata taatccaatt gatcaacgat      780 ggtcctatt tcaacagtca cgaggaacaa ttggaatcaa ccaagaaatt tgaagatgtt       840
ttttcgaaaa ttaatttgaa caagtcactt gggtttagtg actcgatgaa aagaaaaagt      900
gattcaatgc ctatgcatct cccagccaca aagagaataa aagaaaaaca ctcgggcaat     960
cctttgaata aaataaaatt tagcaatttc ttcatgtctg ttaatgacca atacggtatg      1020
aatccaattg ttttgacgat acagcaaaat ggcaatgacg ttaaaagttt gaaattgaaa      1080
gacaatgcta atatttccag taggttccct ggtttaagtg attttaaatc gtgtcctcat      1140
attccaatca ttcacaacat ggtgaaaata ttgctcccgc agttgccaga atcatatagt      1200
atcgacgacg ggtttagttc cagttatgct ttgaagtacg aagaaccaga aaacgcatca     1260
cccacacata ccagtattat atcatctttct agaacttaca gcttgttcac ttgtgtatat    1320
tcctatggta aagagattgt gaaatttgat gaagacggta ttcagttgaa tcaagacaga     1380
gaatttatac cgggattttg gaagttcttc ttcagtacat ttggggatca aagtgaaggt     1440
ggtcttagtg ctgctttcaa aggtgtcacc attaaacaaa tactttacga gtcaagcccc     1500
gatagtgtta aaaggaaaca agatgctagt aaagttaata aactgaaagt caaattggtt    1560
ttactttggg aatttgctaa agtgagtgaa tgcaaagatg ctttgactac tactacaaag    1620
ttggtgttac caccacgagc actggcttca agctcaaaga ccactgaaga agtgtttgaa    1680
tactcagaac cagcattaaa ctcaattggt ggtacccccaa cggacactac tagtcctaat   1740
atggatttga ataatcagaa cttgagtgca gcagcaactt caattcctgg tatacgagac     1800
accattcatt cagcatcaat gccagatatc aatgaattgc catcttcagc taaaccacaa    1860
gtaaggttac aaaagacttt ccaatcgatg caacacttgc aaccacacca aatgtggcaa    1920
caacaacaac aacaacagcc actgcaaggt gcatatacca gctcagtagc ttcacaactg    1980
ctcaatactt cattatcatc accttatgct caatatggca tgccactacc acaacaaaca    2040
ataggcactt tgttccacc tacttcacaa acatttggtg tttcctacac gcataatagc     2100 caacacccttt cagctaatat ggatcttatg atgctttctt ctatgaatac cggatatgga   2160
aatatcacga taatcaaga ttatcaattt ggtaatatag atacacaga aggatttact      2220 agtgagtttt ag                                                        2232
```

<210> SEQ ID NO 4
<211> LENGTH: 743
<212> TYPE: PRT
<213> ORGANISM: Candida albicans

<400> SEQUENCE: 4

Met Met Ser Gln Ala Thr Pro Ser Ala Thr Pro Val Arg Asn Ala Asp
1               5                   10                  15

Gly Gln Lys Lys Gly Lys Lys Leu Pro Leu Ile Val Asp Val Ala Ile
            20                  25                  30

Gly Asn Asn Gly Lys Gln Leu Tyr Gln Val His Glu Ser Ser Lys Met

-continued

```
                 35                  40                  45
Val Arg Lys Glu Met Pro Arg Ser Thr Asn Phe Ala Leu Asn Asp Asp
             50                  55                  60
Ile Ser Asp Glu Gly Phe Phe Ile Ser Gln Ile Asn Glu Gln Arg Thr
 65                  70                  75                  80
Pro Ile Arg Lys Thr Leu Gly Thr Leu Ser Pro Ser Ser Leu Asn Gln
                 85                  90                  95
Lys Arg Ile Arg His Asp Val Tyr Asp Gln Gly Asp Asp Asn Ser Asn
                100                 105                 110
Asp Asp Asn Cys Gln Asn Asp Val Tyr Glu Gln Gln Gln Gln Gln Pro
                115                 120                 125
Gln Gln Gln Gln Gln Gln Gln Gln Leu His Gln Pro Asn Met Tyr
            130                 135                 140
Glu Asn Gly Asn Val Gly Val Ile Ser Asn Asp Pro Val Ser Ser Val
145                 150                 155                 160
Gly His Tyr Asp Asn Asn Pro Val Ser His Val Pro Thr Gly Ala Tyr
                165                 170                 175
Ser Arg Val Gln Asp Thr Asp Ile Trp Ser Asp Asp Val Glu Glu Ala
            180                 185                 190
Phe Glu Glu Val Leu Arg Leu Ile Pro Lys Ser Gly Leu Asn Lys Ile
            195                 200                 205
Lys Ile Ala Gly Arg Ser Cys Gly Arg Asn Glu Leu Ile Ser Asp Tyr
            210                 215                 220
Ile Phe Ala Lys Thr Gly Lys Phe Arg Thr Arg Lys Gln Val Ser Ser
225                 230                 235                 240
His Ile Gln Val Ile Lys Asn Leu Gly Gln Lys Leu Asp Ile Ile Gln
                245                 250                 255
Leu Ile Asn Asp Gly Pro Ile Phe Asn Ser His Glu Glu Gln Leu Glu
            260                 265                 270
Ser Thr Lys Lys Phe Glu Asp Val Phe Ser Lys Ile Asn Leu Asn Lys
            275                 280                 285
Ser Leu Gly Phe Ser Asp Ser Met Lys Arg Lys Ser Asp Ser Met Pro
        290                 295                 300
Met His Leu Pro Ala Thr Lys Arg Ile Arg Arg Lys His Ser Gly Asn
305                 310                 315                 320
Pro Leu Asn Lys Ile Lys Phe Ser Asn Phe Met Ser Val Asn Asp
                325                 330                 335
Gln Tyr Gly Met Asn Pro Ile Val Leu Thr Ile Gln Gln Asn Gly Asn
            340                 345                 350
Asp Val Lys Ser Leu Lys Leu Lys Asp Asn Ala Asn Ile Ser Ser Arg
            355                 360                 365
Phe Pro Gly Leu Ser Asp Phe Lys Ser Cys Pro His Ile Pro Ile Ile
        370                 375                 380
His Asn Met Val Lys Ile Leu Leu Pro Gln Leu Pro Glu Ser Tyr Ser
385                 390                 395                 400
Ile Asp Asp Gly Phe Ser Ser Ser Tyr Ala Leu Lys Tyr Glu Pro
                405                 410                 415
Glu Asn Ala Ser Pro Thr His Thr Ser Ile Ile Ser Ser Ser Arg Thr
            420                 425                 430
Tyr Ser Leu Phe Thr Cys Val Tyr Ser Tyr Gly Lys Glu Ile Val Lys
        435                 440                 445
Phe Asp Glu Asp Gly Ile Gln Leu Asn Gln Asp Arg Glu Phe Ile Pro
        450                 455                 460
```

```
Gly Phe Trp Lys Phe Phe Phe Ser Thr Phe Gly Asp Gln Ser Glu Gly
465                 470                 475                 480

Gly Leu Ser Ala Ala Phe Lys Gly Val Thr Ile Lys Gln Ile Leu Tyr
            485                 490                 495

Glu Ser Ser Pro Asp Ser Val Lys Lys Glu Gln Asp Ala Ser Lys Val
        500                 505                 510

Asn Lys Leu Lys Val Lys Leu Val Leu Leu Trp Glu Phe Ala Lys Val
    515                 520                 525

Ser Glu Cys Lys Asp Ala Leu Thr Thr Thr Lys Leu Val Leu Pro
530                 535                 540

Pro Arg Ala Leu Ala Ser Ser Ser Lys Thr Thr Glu Glu Val Phe Glu
545                 550                 555                 560

Tyr Ser Glu Pro Ala Leu Asn Ser Ile Gly Gly Thr Pro Thr Asp Thr
                565                 570                 575

Thr Ser Pro Asn Met Asp Leu Asn Asn Gln Asn Leu Ser Ala Ala Ala
            580                 585                 590

Thr Ser Ile Pro Gly Ile Arg Asp Thr Ile His Ser Ala Ser Met Pro
        595                 600                 605

Asp Ile Asn Glu Leu Pro Ser Ser Ala Lys Pro Gln Val Arg Leu Gln
    610                 615                 620

Lys Thr Phe Gln Ser Met Gln His Leu Gln Pro His Gln Met Trp Gln
625                 630                 635                 640

Gln Gln Gln Gln Gln Gln Pro Leu Gln Gly Ala Tyr Thr Ser Ser Val
                645                 650                 655

Ala Ser Gln Leu Leu Asn Thr Ser Leu Ser Ser Pro Tyr Ala Gln Tyr
            660                 665                 670

Gly Met Pro Leu Pro Gln Gln Thr Ile Gly Thr Phe Val Pro Pro Thr
        675                 680                 685

Ser Gln Thr Phe Gly Val Ser Tyr Thr His Asn Ser Gln His Pro Ser
690                 695                 700

Ala Asn Met Asp Leu Met Met Leu Ser Ser Met Asn Thr Gly Tyr Gly
705                 710                 715                 720

Asn Ile Thr Asn Asn Gln Asp Tyr Gln Phe Gly Asn Ile Gly Tyr Thr
                725                 730                 735

Glu Gly Phe Thr Ser Glu Phe
            740

<210> SEQ ID NO 5
<211> LENGTH: 1872
<212> TYPE: DNA
<213> ORGANISM: Candida albicans

<400> SEQUENCE: 5
atggcaaaga gaaaactaaa ttcaacaata aagcgcagcc ggacacgttc tggttgcgtt     60
acctgtcgag atagacatat aaaatgcgat gaacaacaac ctgtttgcaa aaactgtcaa    120
aaatcaaatc ggaaatgtta tcgaggaata aggttaaact ttacacaata tacttttac    180 aaccctgatg ataataagcc aaaagaattg caacaaaatg aacagccaaa tagtagtcat    240
tatgcatttc ccaatctaga gccaaatcca gtatcacaaa acataggat attagaccaa    300 tcaataacca ttgcctcatt tatgatgat ttgaaaaagt ataagccata tattcattta    360
catacaccag aagatttaag ggagtcggac ttacaattcc aagaagacac atacaattcg    420
tatatatcca catctgcaat aaatttacgg ggaaaaaaat tgactaaaag agatccgggg    480
```

```
ttgtctactt cattgtcagt tattaatccc acattggaat ctgaaattaa accgaacccg    540
gtgatattga atcaattgag tttccacccc ccaccaaatc ttaatactgg agttttgtat    600
ccaccaaccg caacagcagc aacaacaaca acatcaagtc ctactaatca tcatttacat    660
ccctatttg tcagtctgat accaaatcca caacatcatc caatgctaga cacttctcaa     720
catcaagaga ctacatcaac agaccctaat caattcgatt attcccatct atcaatgcct    780
caatccacac ccttgctaat gaaatacgat atcaccacct atgtaaggtt aattgaaaca    840
gaaaagtatt acatgctatt ggatcttgcc aatgaattag atatttggaa aaaaattata    900
ccgtcattgt gtttgcaaat ttccgagaat gattcattct tgttagattg tttgatgagc    960
tgttctcgta atacatctgt taaccttttg gacttgacta atgaacaatt gaataagtgg    1020
tcgcaattga aaaatgctcc cgtgatatca gaaagaattc aacaatttga acatatacta    1080
ataagtattg tattaatttt acttggatta tatttgaata cgactaaagt tcgactaact    1140
gattatcata aggtgatttt caataatcaa gccaaattgt tttcccacgt attgcgcaag    1200
atccatacat ttatcacatc aaataaaccc aattcggcag tattgacaaa tgccattcaa    1260
tcaattacta tgctcaaatt tttcatagat aaaaattatg acttctcata tgaatttaaa    1320
aatatccaga agggaagagt tactgataca ctggaggaaa tcacgtattc taattcgaat    1380
ttatattcca acccggatat atcctatatt tctacattca acgaatacga gattatctac    1440
ttgaataatt cgtatcagaa tcttgttcac gttgatcaaa gcaatagtat gctgatgggc    1500
gaatctcaat tatacaaaga tctattgtgg tatttgatga agttgatttt tgtcattaat    1560
tatccagaag ctgccaacaa tttggttctt gatcataatg ttgtttatca acaaattact    1620
aatgcatcga ctgatttgag tttcagtaat aacttgaatt atttgaaccc aagatcatat    1680
gcaaattatt ttttgaaaga atttattatc aaagtattga gtatgggtag caatgccatc    1740
attgaagatg ccaataatcg aataaatact ctatttaatt ttattgatca aagctatatg    1800
gacccagaac taaaatcaca atttcatcat tgctttacct ggactgtacg ctacattcac    1860
ccagtaagtg at                                                         1872
```

<210> SEQ ID NO 6
<211> LENGTH: 624
<212> TYPE: PRT
<213> ORGANISM: Candida albicans

<400> SEQUENCE: 6

```
Met Ala Lys Lys Lys Leu Asn Ser Thr Ile Lys Arg Ser Arg Thr Arg
 1               5                  10                  15

Ser Gly Cys Val Thr Cys Arg Asp Arg His Ile Lys Cys Asp Glu Gln
            20                  25                  30

Gln Pro Val Cys Lys Asn Cys Gln Lys Ser Asn Arg Lys Cys Tyr Arg
        35                  40                  45

Gly Ile Arg Leu Asn Phe Thr Gln Tyr Thr Phe Tyr Asn Pro Asp Asp
    50                  55                  60

Asn Lys Pro Lys Glu Leu Gln Gln Asn Glu Gln Pro Asn Ser Ser His
65                  70                  75                  80

Tyr Ala Phe Pro Asn Leu Glu Pro Asn Pro Val Ser Gln Lys His Arg
                85                  90                  95

Ile Leu Asp Gln Ser Ile Thr Ile Ala Ser Leu Tyr Asp Asp Leu Lys
            100                 105                 110

Lys Tyr Lys Pro Tyr Ile His Leu His Thr Pro Glu Asp Leu Arg Glu
        115                 120                 125
```

-continued

```
Ser Asp Leu Gln Phe Gln Glu Asp Thr Tyr Asn Ser Tyr Ile Ser Thr
    130                 135                 140

Ser Ala Ile Asn Leu Arg Gly Lys Lys Leu Thr Lys Arg Asp Pro Gly
145                 150                 155                 160

Leu Ser Thr Ser Leu Ser Val Ile Asn Pro Thr Leu Glu Ser Glu Ile
                165                 170                 175

Lys Pro Asn Pro Val Ile Leu Asn Gln Leu Ser Phe His Pro Pro
            180                 185                 190

Asn Leu Asn Thr Gly Val Leu Tyr Pro Pro Thr Ala Thr Ala Ala Thr
        195                 200                 205

Thr Thr Thr Ser Ser Pro Thr Asn His His Leu His Pro Tyr Phe Val
    210                 215                 220

Ser Leu Ile Pro Asn Pro Gln His His Pro Met Leu Asp Thr Ser Gln
225                 230                 235                 240

His Gln Glu Thr Thr Ser Thr Asp Pro Asn Gln Phe Asp Tyr Ser His
                245                 250                 255

Leu Ser Met Pro Gln Ser Thr Pro Leu Leu Met Lys Tyr Asp Ile Thr
            260                 265                 270

Thr Tyr Val Arg Leu Ile Glu Thr Glu Lys Tyr Tyr Met Leu Leu Asp
        275                 280                 285

Leu Ala Asn Glu Leu Asp Ile Trp Lys Lys Ile Pro Ser Leu Cys
    290                 295                 300

Leu Gln Ile Ser Glu Asn Asp Ser Phe Leu Leu Asp Cys Leu Met Ser
305                 310                 315                 320

Cys Ser Arg Asn Thr Ser Val Asn Leu Leu Asp Leu Thr Asn Glu Gln
                325                 330                 335

Leu Asn Lys Trp Ser Gln Leu Lys Asn Ala Pro Val Ile Ser Glu Arg
            340                 345                 350

Ile Gln Gln Phe Glu His Ile Leu Ile Ser Ile Val Leu Ile Leu Leu
        355                 360                 365

Gly Leu Tyr Leu Asn Thr Thr Lys Val Arg Leu Thr Asp Tyr His Lys
    370                 375                 380

Val Ile Phe Asn Asn Gln Ala Lys Leu Phe Ser His Val Leu Arg Lys
385                 390                 395                 400

Ile His Thr Phe Ile Thr Ser Asn Lys Pro Asn Ser Ala Val Leu Thr
                405                 410                 415

Asn Ala Ile Gln Ser Ile Thr Met Leu Lys Phe Phe Ile Asp Lys Asn
            420                 425                 430

Tyr Asp Phe Ser Tyr Glu Phe Lys Asn Ile Gln Lys Gly Arg Val Thr
        435                 440                 445

Asp Thr Leu Glu Glu Ile Thr Tyr Ser Asn Ser Asn Leu Tyr Ser Asn
    450                 455                 460

Pro Asp Ile Ser Tyr Ile Ser Thr Phe Asn Glu Tyr Glu Ile Ile Tyr
465                 470                 475                 480

Leu Asn Asn Ser Tyr Gln Asn Leu Val His Val Asp Gln Ser Asn Ser
                485                 490                 495

Met Leu Met Gly Glu Ser Gln Leu Tyr Lys Asp Leu Leu Trp Tyr Leu
            500                 505                 510

Met Lys Val Asp Phe Val Ile Asn Tyr Pro Glu Ala Ala Asn Asn Leu
        515                 520                 525

Val Leu Asp His Asn Val Val Tyr Gln Gln Ile Thr Asn Ala Ser Thr
    530                 535                 540
```

```
Asp Leu Ser Phe Ser Asn Asn Leu Asn Tyr Leu Asn Pro Arg Ser Tyr
545                 550                 555                 560

Ala Asn Tyr Phe Leu Lys Glu Phe Ile Ile Lys Val Leu Ser Met Gly
                565                 570                 575

Ser Asn Ala Ile Ile Glu Asp Ala Asn Asn Arg Ile Asn Thr Leu Phe
                580                 585                 590

Asn Phe Ile Asp Gln Ser Tyr Met Asp Pro Glu Leu Lys Ser Gln Phe
            595                 600                 605

His His Cys Phe Thr Trp Thr Val Arg Tyr Ile His Pro Val Ser Asp
        610                 615                 620
```

<210> SEQ ID NO 7
<211> LENGTH: 80
<212> TYPE: DNA
<213> ORGANISM: Artificial Sequence
<220> FEATURE:
<223> OTHER INFORMATION: Primer

<400> SEQUENCE: 7

```
gaattcgcct ttttaccctt tttactattg gattctttct tcgatttctt attgcccatt    60
tgtggaattg tgagcggata                                                80
```

<210> SEQ ID NO 8
<211> LENGTH: 80
<212> TYPE: DNA
<213> ORGANISM: Artificial Sequence
<220> FEATURE:
<223> OTHER INFORMATION: Primer

<400> SEQUENCE: 8

```
gctatatttt gttgctttta ttaatttatt ggcttttttat tttgttttgg tttgttttgt    60
gttttcccag tcacgacgtt                                                80
```

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9

```
cgaacagtat atcaaactgc acttt                                          25
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10

```
atggctggaa atccttcttt                                                20
```

<210> SEQ ID NO 11
<211> LENGTH: 81
<212> TYPE: DNA
<213> ORGANISM: Artificial Sequence
<220> FEATURE:
<223> OTHER INFORMATION: Primer

<400> SEQUENCE: 11

```
taattcacgt gtccaagaca ctgacatctg tccagatgat gatgaagaag cttttgaaga    60
```

```
agttttccca gtcacgacgt t                                              81
```

```
<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
catcaaccta atatgtatga gaacg                                          25

<210> SEQ ID NO 13
<211> LENGTH: 81
<212> TYPE: DNA
<213> ORGANISM: Artificial Sequence
<220> FEATURE:
<223> OTHER INFORMATION: Primer

<400> SEQUENCE: 13
tcattgatat ctggcattga tgctgaatga atggtgtctc gtataccagg aattgaagtt    60
gtgtggaatt gtgagcggat a                                              81

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tttggtgtgg ttgcaagtgt                                                20

<210> SEQ ID NO 15
<211> LENGTH: 85
<212> TYPE: DNA
<213> ORGANISM: Artificial Sequence
<220> FEATURE:
<223> OTHER INFORMATION: Primer

<400> SEQUENCE: 15 acataaatt ctttcatatt ttcattttat ttcatacgtt aagatccata tccaatagtc    60
atgggttttc ccaagtcacg acgtt                                          85

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ggtaaaaaac cttcatttaa                                                20

<210> SEQ ID NO 17
<211> LENGTH: 80
<212> TYPE: DNA
<213> ORGANISM: Artificial Sequence
<220> FEATURE:
<223> OTHER INFORMATION: Primer

<400> SEQUENCE: 17
cggtagtaaa aatatatcta tatctcaaag cgtggaaata tattcccact cgtccaaagt    60
tgtggaattg tgagcggata                                                80
```

-continued

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
agaaaaatac aaagccaatt                                                  20

<210> SEQ ID NO 19
<211> LENGTH: 2448
<212> TYPE: DNA
<213> ORGANISM: Candida albicans

<400> SEQUENCE: 19

```
ctaatctcca ttttcaattg gatctgcagc ccaattcatt cccatgaagt tatcatcatc        60
ggtaccgcca gcacctcctg aacccgaacc agtgccagta atatcacctc ctggtccagt       120
agttgtccat atatcatcaa gactatcaat gttgaaatta atgtcaaatg catgagtcga       180
atcaccaaat accagattat tcattcccat tcctgggcca cttacactga gattattact       240
tccatttgaa agattttgcc cacgattatg attgctgttg ttgctatttt gttggtgatg       300
atgttgtgta tctaataaat gaacatcaaa tggatcgtcg ttaaatgtat tggacatagc       360
agtggcttga gttggtgcca atgggggggtt taaatctaga tcttgatctt gtaacgaagt       420
tgaagattct ttcttcaaag ataatactcc attctcttct tcttttatta taggatctaa       480
gttttttggag tttgcattgg ttttggcttg cttctttgga gaattgccat tactattttc       540
attattgtca ttcaatttac ctgatttacg cttctttttc gtagtttcac cgctaattgg       600
ttcagagcga ggtgtcaatg gctggaaatc cttctttccc atacttggag tatttgaacc       660
tggacgctgt tgcttgtctt gtaattgacg catttgctct gttggttgag gctgcttttg       720
ctccgtgcca gcactaggag gttgtgacat gtttggtgtt gtttgtccag atgttttgtt       780
gtttgctgtt gtagaagcat ttgaattcgc cttttttaccc tttttactat tggattcttt       840
cttcgatttc ttattgccca ttgctggtga tgatttattg cctaatgcag gtgaattgtt       900
tgacgttgca ggtgatggtt tttgattaaa ttgtccctga ggaccatttg cagttgttgg       960
cggaggtggt gggtggaaag ttgctggagt tggttgttgt tgattaggag gaagttgatt      1020
ttgattttga tttgaatttg aatattgatt ttgaccggca aacatcattc cattactcaa      1080
tgggttggag tcggaattac cagtgttcct agcaaattct aatctctctt tattctgtct      1140
ttctaataac attaattgat tttgataatc tcgtagagca ttattgtttc tgccactact      1200
gttattacta gtgccgtttg acatctgacc attctttttc attccttgag acccagccat      1260
cttagtcatt tgctgttgtt gttgttgatg gctctggaag ttatgttgag cttgtgcttg      1320
accttgttga gaaggatgtg gcagtgaagc tggtgcagca ttttgttgtg gagtcagctg      1380
ttgatttgat cttgcaccaa caggagagtt attcttcaga gatgaatcac ccattgctga      1440
tgtcaaattg ccttgcaact gaccctgttg ttgttgctgt tgctgttgct gttgctgctg      1500
ctgagcaacc attgcagctt gttgacgcaa attgttcatt tgattttgtg cttgttgctg      1560
gaaagtagtt ttgggttgct gctgctgctg ttgttgttgt aaaaatagtt gttgttgcaa      1620
attcaaatta ccaggtccac cacctacagc attcatcatt tgctgttgtt gttgtggatc      1680
taaaccattc attgggattt gttgtctttg tgcagccatt gcttgttgtt tcatcatcat      1740
```

```
tgccattctt tgttgttgtt ccattgaagg ctgattttga ccatttggca tctgagcaaa      1800
ttgttgatta atggggaaca tttgttgttg aggattcaga tttggtggca tattgatagg      1860
gaaattagcg ttagttgcag aacctggcgg ttgaggtgtt tgacctggtc cttgaggttg      1920
gccttgatgc tgtgggcaa attgatgttg ttgattttgc ataccactag caacaccgat       1980
tcctctttgc tgttgctgca ggaaaggctg tccctgttgc ccttgttgtt gctgttgttg      2040
ttgaaagtga tgttgttgtt gttgctgctg ctgtataaga ggaagttgac tgaaaagatg      2100
tttttgagtt tcttggactc tgagataatc atgataaagc ttgttgttag ggttattatt      2160
actgttaccg tctccatatc tgacttgaaa taaatcaaag aaaacttgcc accattccaa      2220
taaaaatcct tgagaacaat ccatcaaagg aggaatagaa ggcaaattgg gactttcttt      2280
agaaaatgct tttgctgtat cttgaaattg atgtttgacc aaaaaatcca aaatcaacga      2340
gtttaaaacc tgtttagttg tgttgggaac catagtattg gatgatgatg gagttgctgt      2400
tgttgttgat atcggttcat tttctggtag tacttgttta tgattcat                  2448

<210> SEQ ID NO 20
<211> LENGTH: 2232
<212> TYPE: DNA
<213> ORGANISM: Candida albicans

<400> SEQUENCE: 20
ctaaaactca ctagtaaatc cttctgtgta tcctatatta ccaaattgat aatcttgatt       60
attcgtgata tttccatatc cggtattcat agaagaaagc atcataagat ccatattagc      120
tgaagggtgt tggctattat gcgtgtagga acaccaaat gtttgtgaag taggtggaac       180
aaaagtgcct attgtttgtt gtggtagtgg catgccatat tgagcataag gtgatgataa      240
tgaagtattg agcagttgtg aagctactga gctggtatat gcaccttgca gtggctgttg      300
ttgttgttgt tgttgccaca tttggtgtgg ttgcaagtgt tgcatcgatt ggaaagtctt      360
ttgtaacctt acttgtggtt tagctgaaga tggcaattca ttgatatctg gcattgatgc      420
tgaatgaatg gtgtctcgta taccaggaat tgaagttgct gctgcactca agttctgatt      480
attcaaatcc atattaggac tagtagtgtc cgttggggta ccaccaattg agtttaatgc      540
tggttctgag tattcaaaca cttcttcagt ggtctttgag cttgaagcca gtgctcgtgg      600
tggtaacacc aactttgtag tagtagtcaa agcatctttg cattcactca ctttagcaaa      660
ttcccaaagt aaaaccaatt tgactttcag tttattaact ttactagcat cttgttcctt      720
tttaacacta tcgggcttg actcgtaaag tatttgttta atggtgacac cttttgaaagc      780 agcactaaga ccaccttcac tttgatcccc aaatgtactg aagaagaact tccaaaatcc      840
cggtataaat tctctgtctt gattcaactg aataccgtct tcatcaaatt tcacaatctc      900
tttaccatag gaatatacac aagtgaacaa gctgtaagtt ctagaagatg atataatact      960
ggtatgtgtg ggtgatgcgt tttctggttc ttcgtacttc aaagcataac tggaactaaa     1020
cccgtcgtcg atactatatg attctggcaa ctgcgggagc aatattttca ccatgttgtg     1080
aatgattgga atatgaggac acgatttaaa atcacttaaa ccagggaacc tactggaaat     1140
attagcattg tctttcaatt tcaaactttt aacgtcattg ccattttgct gtatcgtcaa     1200
aacaattgga ttcataccgt attggtcatt aacagacatg aagaaattgc taaattttat     1260
tttattcaaa ggattgcccg agtgttttct tcttattctc tttgtggctg ggagatgcat     1320
aggcattgaa tcacttttc ttttcatcga gtcactaaac ccaagtgact tgttcaaatt     1380
aattttcgaa aaaacatctt caaatttctt ggttgattcc aattgttcct cgtgactgtt     1440
```

-continued

```
gaaaatagga ccatcgttga tcaattggat tatatcgagt ttttgtccta aattcttaat    1500
cacttgaatg tgagaggaca cttgctttct tgttctgaat tcccggtttt ggcaaaaat    1560 gtaatctgat attaattcat ttctaccaca agatctaccg gcaatcttta ttttgttcaa    1620
accactcttt ggaataagtc tcaacacttc ttcaaaagct tcttcaacat catctgacca    1680
gatgtcagtg tcttggacac gtgaataagc accagtaggt acatgtgaaa ctgggttgtt    1740
gtcatagtgg ccaacagaag acactggatc attggaaata accccaacgt tgccgttctc    1800
atacatatta ggttgatgaa gttgttgttg ttgttgttgt tgttgctgtg gttgttgttg    1860
ttgttgctca taaacatcat tttggcaatt atcgtcattg ctattgtcat ctccttggtc    1920
gtacacatca tggcggattc tcttttggtt gagactagat ggagacaaag tacccaaagt    1980 cttttctaatg ggagttcttt gttcatttat ttggcttata aaaaacccctt catcagaaat    2040 gtcatcattc aaagcaaaat tggtagatct tggcatttcc tttcttacca tcttggaaga    2100
ttcgtgtacc tggtaaagtt gcttaccatt attaccaatt gcaacatcaa caattaatgg    2160
aagcttcttg cctttctttt gtccatcggc atttctcacg ggagtagcac taggagtagc    2220
ttgcgacatc at                                                          2232
```

<210> SEQ ID NO 21
<211> LENGTH: 1872
<212> TYPE: DNA
<213> ORGANISM: Candida albicans

<400> SEQUENCE: 21

```
atcacttact gggtgaatgt agcgtacagt ccaggtaaag caatgatgaa attgtgattt      60
tagttctggg tccatatagc tttgatcaat aaaattaaat agagtattta ttcgattatt     120
ggcatcttca atgatggcat tgctacccat actcaatact ttgataataa attctttcaa     180
aaaataattt gcatatgatc ttgggttcaa ataattcaag ttattactga aactcaaatc     240
agtcgatgca ttagtaattt gttgataaac aacattatga tcaagaacca aattgttggc     300
agcttctgga taattaatga caaaatcaac tttcatcaaa taccacaata gatctttgta     360
taattgagat tcgcccatca gcatactatt gctttgatca acgtgaacaa gattctgata     420
cgaattattc aagtagataa tctcgtattc gttgaatgta gaaatatagg atatatccgg     480
gttggaatat aaattcgaat tagaatacgt gatttcctcc agtgtatcag taactcttcc     540
cttctggata ttttttaaatt catatgagaa gtcataattt ttatctatga aaaatttgag     600
catagtaatt gattgaatgg catttgtcaa tactgccgaa ttgggtttat ttgatgtgat     660
aaatgtatgg atcttgcgca atacgtggga aaacaatttg gcttgattat tgaaaatcac     720
cttatgataa tcagttagtc gaactttagt cgtattcaaa tataatccaa gtaaaattaa     780
tacaatactt attagtatat gttcaaattg ttgaattctt tctgatatca cgggagcatt     840
tttcaattgc gaccacttat tcaattgttc attagtcaag tccaaaaggt taacagatgt     900
attacgagaa cagctcatca aacaatctaa caagaatgaa tcattctcgg aaatttgcaa     960
acacaatgac ggtataattt ttttccaaat atctaattca ttggcaagat ccaatagcat    1020
gtaatacttt tctgtttcaa ttaaccttac ataggtggtg atatcgtatt tcattagcaa    1080
gggtgtggat tgaggcattg atagatggga ataatcgaat tgattagggt ctgttgatgt    1140
agtctcttga tgttgagaag tgtctagcat tggatgatgt tgtggatttg gtatcagact    1200
gacaaaatag ggatgtaaat gatgattagt aggacttgat gttgttgttg ttgctgctgt    1260
```

```
tgcggttggt ggatacaaaa ctccagtatt aagatttggt gggggggtgga aactcaattg    1320 attcaatatc accgggttcg gtttaatttc agattccaat gtgggattaa taactgacaa    1380
tgaagtagac aaccccggat ctcttttagt caatttttt ccccgtaaat ttattgcaga     1440
tgtggatata tacgaattgt atgtgtcttc ttggaattgt aagtccgact cccttaaatc   1500
ttctggtgta tgtaaatgaa tatatggctt atacttttc aaatcatcat ataatgaggc    1560
aatggttatt gattggtcta atatcctatg tttttgtgat actggatttg gctctagatt   1620
gggaaatgca taatgactac tatttggctg ttcattttgt tgcaattctt ttggcttatt   1680
atcatcaggg ttgtaaaaag tatattgtgt aaagtttaac cttattcctc gataacattt   1740
ccgatttgat ttttgacagt ttttgcaaac aggttgttgt tcatcgcatt ttatatgtct   1800
atctcgacag gtaacgcaac cagaacgtgt ccggctgcgc tttattgttg aatttagttt   1860
cttctttgcc at                                                        1872
```